US008147441B2

(12) United States Patent
Gannoe et al.

(10) Patent No.: US 8,147,441 B2
(45) Date of Patent: Apr. 3, 2012

(54) METHOD AND DEVICE FOR USE IN ENDOSCOPIC ORGAN PROCEDURES

(75) Inventors: Jamy Gannoe, Redwood City, CA (US);
Craig Gerbi, Mountain View, CA (US);
Gary Weller, Los Gatos, CA (US);
Matthew J. Collier, Los Altos, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 822 days.

(21) Appl. No.: 11/713,852

(22) Filed: Mar. 5, 2007

(65) Prior Publication Data
US 2007/0156159 A1 Jul. 5, 2007

Related U.S. Application Data

(63) Continuation of application No. 10/351,231, filed on Jan. 24, 2003, now Pat. No. 7,220,237, which is a continuation-in-part of application No. 10/279,257, filed on Oct. 23, 2002, now Pat. No. 7,229,428.

(51) Int. Cl.
*A61M 5/00* (2006.01)
*A61B 17/08* (2006.01)

(52) U.S. Cl. .......................... 604/8; 606/153

(58) Field of Classification Search ............ 604/7–10, 604/19, 27–29, 48, 500, 506–508, 264, 523, 604/533, 540; 606/8, 108, 139, 140, 151–159, 606/219–220; 128/898–899; 623/11.11, 623/23.64–23.68, 23.7, 23.71, 23.75, 23.76
See application file for complete search history.

(56) References Cited

U.S. PATENT DOCUMENTS
2,108,206 A 2/1938 Meeker
(Continued)

FOREIGN PATENT DOCUMENTS
EP 0 137 878 A1 4/1985
(Continued)

OTHER PUBLICATIONS

Benjamin, S.B., et al., *A Double-Blind Cross Over Study of the Garren-Edwards anti-Obesity Bubblern* Abstract, Submitted to AIS/G/EII987, Georgetown University Hospital and Fairfax Hospital, Washington, D.C. and Fairfax, VA.

(Continued)

*Primary Examiner* — Leslie Deak
*Assistant Examiner* — Philip R Wiest
(74) *Attorney, Agent, or Firm* — Nutter McClennen & Fish LLP

(57) ABSTRACT

Methods and devices for use in tissue approximation and fixation are described herein. The present invention provides, in part, methods and devices for acquiring tissue folds in a circumferential configuration within a hollow body organ, e.g., a stomach, positioning the tissue folds for affixing within a fixation zone of the stomach, preferably to create a pouch or partition below the esophagus, and fastening the tissue folds such that a tissue ring, or stomas, forms excluding the pouch from the greater stomach cavity. The present invention further provides for a liner or bypass conduit which is affixed at a proximal end either to the tissue ring or through some other fastening mechanism. The distal end of the conduit is left either unanchored or anchored within the intestinal tract. This bypass conduit also includes a fluid bypass conduit which allows the stomach and a portion of the intestinal tract to communicate.

11 Claims, 30 Drawing Sheets

U.S. PATENT DOCUMENTS

| | | |
|---|---|---|
| 2,508,690 A | 7/1948 | Schmerl |
| 3,372,443 A | 2/1967 | Daddona, Jr. |
| 3,395,710 A | 8/1968 | Stratton et al. |
| 3,986,493 A | 10/1976 | Hendren, III |
| 4,057,065 A | 11/1977 | Thow |
| 4,063,561 A | 12/1977 | McKenna |
| 4,133,315 A | 1/1979 | Berman et al. |
| 4,134,405 A | 1/1979 | Smit |
| 4,198,982 A | 4/1980 | Fortner et al. |
| 4,246,893 A | 1/1981 | Berson |
| 4,258,705 A | 3/1981 | Sorensen et al. |
| 4,311,146 A | 1/1982 | Wonder |
| 4,315,509 A | 2/1982 | Smit |
| 4,343,066 A | 8/1982 | Lance |
| 4,402,445 A | 9/1983 | Green |
| 4,416,267 A | 11/1983 | Garren et al. |
| 4,458,681 A | 7/1984 | Hopkins |
| 4,485,805 A | 12/1984 | Foster, Jr. |
| 4,488,523 A | 12/1984 | Shichman |
| 4,501,264 A | 2/1985 | Rockey |
| 4,547,192 A | 10/1985 | Brodsky et al. |
| 4,558,699 A | 12/1985 | Bashour |
| 4,592,339 A | 6/1986 | Kuzmak et al. |
| 4,592,354 A | 6/1986 | Rothfuss |
| 4,598,699 A | 7/1986 | Garren et al. |
| 4,607,618 A | 8/1986 | Angelchik |
| 4,610,383 A | 9/1986 | Rothfuss et al. |
| 4,636,205 A | 1/1987 | Steer |
| 4,641,653 A | 2/1987 | Rockey |
| 4,643,169 A | 2/1987 | Koss et al. |
| 4,646,722 A | 3/1987 | Silverstein et al. |
| 4,648,383 A | 3/1987 | Angelchik |
| 4,671,287 A | 6/1987 | Fiddian-Green |
| 4,671,445 A | 6/1987 | Barker et al. |
| 4,694,827 A | 9/1987 | Weiner et al. |
| 4,696,288 A | 9/1987 | Kuzmak |
| 4,716,900 A | 1/1988 | Ravo et al. |
| 4,723,547 A | 2/1988 | Kullas et al. |
| 4,739,758 A | 4/1988 | Lai et al. |
| 4,744,363 A | 5/1988 | Hasson |
| 4,754,909 A | 7/1988 | Barker et al. |
| 4,773,393 A | 9/1988 | Haber et al. |
| 4,790,294 A | 12/1988 | Allred, III et al. |
| 4,795,430 A | 1/1989 | Quinn et al. |
| 4,803,985 A | 2/1989 | Hill |
| 4,841,888 A | 6/1989 | Mills et al. |
| 4,899,747 A | 2/1990 | Garren et al. |
| 4,905,693 A | 3/1990 | Ravo |
| 4,925,446 A | 5/1990 | Garay et al. |
| 4,927,428 A | 5/1990 | Richards |
| 4,969,474 A | 11/1990 | Schwarz |
| 5,037,021 A | 8/1991 | Mills et al. |
| 5,059,193 A | 10/1991 | Kuslich |
| 5,080,663 A | 1/1992 | Mills et al. |
| 5,084,061 A | 1/1992 | Gau et al. |
| 5,112,310 A | 5/1992 | Grobe |
| 5,129,915 A | 7/1992 | Cantenys |
| 5,146,933 A | 9/1992 | Boyd |
| 5,156,609 A | 10/1992 | Nakao et al. |
| 5,171,233 A | 12/1992 | Amplatz et al. |
| 5,197,649 A | 3/1993 | Bessler et al. |
| 5,220,928 A | 6/1993 | Oddsen et al. |
| 5,222,961 A | 6/1993 | Nakao et al. |
| 5,226,429 A | 7/1993 | Kuzmak |
| 5,234,454 A | 8/1993 | Bangs |
| 5,246,456 A | 9/1993 | Wilkinson |
| 5,248,302 A | 9/1993 | Patrick et al. |
| 5,250,058 A | 10/1993 | Miller et al. |
| 5,254,126 A | 10/1993 | Filipi et al. |
| 5,259,366 A | 11/1993 | Reydel et al. |
| 5,259,399 A | 11/1993 | Brown |
| 5,261,920 A | 11/1993 | Main et al. |
| 5,263,629 A | 11/1993 | Trumbull et al. |
| 5,284,128 A | 2/1994 | Hart |
| 5,297,536 A | 3/1994 | Wilk |
| 5,301,658 A | 4/1994 | Zhu et al. |
| 5,306,300 A | 4/1994 | Berry |
| 5,309,896 A | 5/1994 | Moll et al. |
| 5,309,927 A | 5/1994 | Welch |
| 5,327,914 A | 7/1994 | Shlain |
| 5,330,486 A | 7/1994 | Wilk |
| 5,330,503 A | 7/1994 | Yoon |
| 5,331,975 A | 7/1994 | Bonutti |
| 5,334,209 A | 8/1994 | Yoon |
| 5,334,210 A | 8/1994 | Gianturco |
| 5,345,949 A | 9/1994 | Shlain |
| 5,346,501 A | 9/1994 | Regula et al. |
| 5,350,104 A | 9/1994 | Main et al. |
| 5,355,897 A | 10/1994 | Pietrafitta et al. |
| 5,376,095 A | 12/1994 | Ortiz |
| 5,382,231 A | 1/1995 | Shlain |
| 5,395,030 A | 3/1995 | Kuramoto et al. |
| 5,403,312 A | 4/1995 | Yates et al. |
| 5,403,326 A | 4/1995 | Harrison et al. |
| 5,411,508 A | 5/1995 | Bessler et al. |
| 5,433,721 A | 7/1995 | Hooven et al. |
| 5,437,291 A | 8/1995 | Pasricha et al. |
| 5,449,368 A | 9/1995 | Kuzmak |
| 5,452,837 A | 9/1995 | Williamson, IV et al. |
| 5,458,131 A | 10/1995 | Wilk |
| 5,462,559 A | 10/1995 | Ahmed |
| 5,465,894 A | 11/1995 | Clark et al. |
| 5,467,911 A | 11/1995 | Tsuruta et al. |
| 5,486,183 A | 1/1996 | Middleman et al. |
| 5,489,058 A | 2/1996 | Plyley et al. |
| 5,503,635 A | 4/1996 | Sauer et al. |
| 5,527,319 A | 6/1996 | Green et al. |
| 5,535,935 A | 7/1996 | Vidal et al. |
| 5,542,949 A | 8/1996 | Yoon |
| 5,549,621 A | 8/1996 | Bessler et al. |
| 5,551,622 A | 9/1996 | Yoon |
| 5,555,898 A | 9/1996 | Suzuki et al. |
| 5,558,665 A | 9/1996 | Kieturakis |
| 5,571,116 A | 11/1996 | Bolanos et al. |
| 5,577,654 A | 11/1996 | Bishop |
| 5,578,044 A | 11/1996 | Gordon et al. |
| 5,582,616 A | 12/1996 | Bolduc et al. |
| 5,584,861 A | 12/1996 | Swain et al. |
| 5,588,579 A | 12/1996 | Schnut et al. |
| 5,601,604 A | 2/1997 | Vincent |
| 5,603,443 A | 2/1997 | Clark et al. |
| 5,607,094 A | 3/1997 | Clark et al. |
| 5,624,381 A | 4/1997 | Kieturakis |
| 5,626,588 A | 5/1997 | Sauer et al. |
| 5,639,008 A | 6/1997 | Gallagher et al. |
| 5,649,937 A | 7/1997 | Bito et al. |
| 5,651,769 A | 7/1997 | Waxman et al. |
| 5,655,698 A | 8/1997 | Yoon |
| 5,662,664 A | 9/1997 | Gordon et al. |
| 5,662,667 A | 9/1997 | Knodel |
| 5,667,520 A | 9/1997 | Bonutti |
| 5,676,659 A | 10/1997 | McGurk |
| 5,676,674 A | 10/1997 | Bolanos et al. |
| 5,685,868 A | 11/1997 | Lundquist |
| 5,690,656 A | 11/1997 | Cope et al. |
| 5,697,943 A | 12/1997 | Sauer et al. |
| 5,707,382 A | 1/1998 | Sierocuk et al. |
| 5,722,990 A | 3/1998 | Sugarbaker et al. |
| 5,728,178 A | 3/1998 | Buffington et al. |
| 5,735,848 A | 4/1998 | Yates et al. |
| 5,749,893 A | 5/1998 | Vidal et al. |
| 5,755,730 A | 5/1998 | Swain et al. |
| 5,766,216 A | 6/1998 | Gangal et al. |
| 5,776,054 A | 7/1998 | Bobra |
| 5,782,844 A | 7/1998 | Yoon et al. |
| 5,788,715 A | 8/1998 | Watson, Jr. et al. |
| 5,792,153 A | 8/1998 | Swain et al. |
| 5,797,931 A | 8/1998 | Bito et al. |
| 5,799,857 A | 9/1998 | Robertson et al. |
| 5,810,851 A | 9/1998 | Yoon |
| 5,810,855 A | 9/1998 | Rayburn et al. |
| 5,810,882 A | 9/1998 | Bolduc et al. |
| 5,816,471 A | 10/1998 | Plyley et al. |
| 5,820,584 A | 10/1998 | Crabb |
| 5,824,008 A | 10/1998 | Bolduc et al. |
| 5,827,298 A | 10/1998 | Hart et al. |
| 5,833,690 A | 11/1998 | Yates et al. |

| | | | |
|---|---|---|---|
| 5,836,311 A | 11/1998 | Borst et al. | |
| 5,839,639 A * | 11/1998 | Sauer et al. ............... 227/175.1 | |
| 5,855,312 A | 1/1999 | Toledano | |
| 5,860,581 A | 1/1999 | Robertson et al. | |
| 5,861,036 A | 1/1999 | Godin | |
| 5,868,141 A | 2/1999 | Ellias | |
| 5,868,760 A | 2/1999 | McGuckin, Jr. | |
| 5,876,448 A | 3/1999 | Thompson et al. | |
| 5,879,371 A | 3/1999 | Gardiner et al. | |
| 5,887,594 A | 3/1999 | LoCicero, III | |
| 5,888,196 A | 3/1999 | Bonutti | |
| 5,897,534 A | 4/1999 | Heim et al. | |
| 5,897,562 A | 4/1999 | Bolanos et al. | |
| 5,904,147 A | 5/1999 | Conlan et al. | |
| 5,906,625 A | 5/1999 | Bito et al. | |
| 5,910,105 A | 6/1999 | Swain et al. | |
| 5,910,149 A | 6/1999 | Kuzmak | |
| 5,921,993 A | 7/1999 | Yoon | |
| 5,927,284 A | 7/1999 | Borst et al. | |
| 5,928,264 A | 7/1999 | Sugarbaker et al. | |
| 5,935,107 A | 8/1999 | Taylor et al. | |
| 5,938,669 A | 8/1999 | Klaiber et al. | |
| 5,947,983 A | 9/1999 | Solar et al. | |
| 5,964,772 A | 10/1999 | Bolduc et al. | |
| 5,964,782 A | 10/1999 | Lafontaine et al. | |
| 5,972,001 A | 10/1999 | Yoon | |
| 5,972,002 A | 10/1999 | Bark et al. | |
| 5,976,161 A * | 11/1999 | Kirsch et al. ............... 606/149 | |
| 5,980,537 A | 11/1999 | Ouchi | |
| 5,993,464 A | 11/1999 | Knodel | |
| 5,993,473 A | 11/1999 | Chan et al. | |
| 6,015,378 A | 1/2000 | Borst et al. | |
| 6,030,364 A | 2/2000 | Durgin et al. | |
| 6,030,392 A | 2/2000 | Dakov | |
| 6,042,538 A | 3/2000 | Puskas | |
| 6,044,847 A | 4/2000 | Carter et al. | |
| 6,067,991 A | 5/2000 | Forsell | |
| 6,074,343 A | 6/2000 | Nathanson et al. | |
| 6,083,241 A | 7/2000 | Longo et al. | |
| 6,086,600 A | 7/2000 | Kortenbach | |
| 6,113,609 A | 9/2000 | Adams | |
| 6,119,913 A | 9/2000 | Adams et al. | |
| 6,120,513 A | 9/2000 | Bailey et al. | |
| 6,136,006 A | 10/2000 | Johnson et al. | |
| 6,159,146 A | 12/2000 | El Gazayerli | |
| 6,159,195 A | 12/2000 | Ha et al. | |
| 6,165,183 A | 12/2000 | Kuehn et al. | |
| 6,179,195 B1 | 1/2001 | Adams et al. | |
| 6,186,942 B1 | 2/2001 | Sullivan et al. | |
| 6,186,985 B1 | 2/2001 | Snow | |
| 6,197,022 B1 * | 3/2001 | Baker ............... 606/33 | |
| 6,200,318 B1 | 3/2001 | Har-Shai et al. | |
| 6,206,822 B1 | 3/2001 | Foley et al. | |
| 6,206,893 B1 | 3/2001 | Klein et al. | |
| 6,224,614 B1 | 5/2001 | Yoon | |
| 6,231,561 B1 | 5/2001 | Frazier et al. | |
| 6,248,058 B1 | 6/2001 | Silverman et al. | |
| 6,254,642 B1 * | 7/2001 | Taylor ............... 623/23.64 | |
| 6,273,897 B1 | 8/2001 | Dalessandro et al. | |
| 6,279,809 B1 | 8/2001 | Nicolo | |
| 6,290,674 B1 | 9/2001 | Roue et al. | |
| 6,293,923 B1 | 9/2001 | Yachia et al. | |
| 6,302,917 B1 | 10/2001 | Dua et al. | |
| 6,312,437 B1 | 11/2001 | Kortenbach | |
| 6,328,689 B1 | 12/2001 | Gonzalez et al. | |
| 6,338,345 B1 | 1/2002 | Johnson et al. | |
| 6,338,737 B1 | 1/2002 | Toledano | |
| 6,352,543 B1 | 3/2002 | Cole | |
| 6,358,197 B1 | 3/2002 | Silverman et al. | |
| 6,379,366 B1 | 4/2002 | Fleischmann et al. | |
| 6,387,104 B1 | 5/2002 | Pugsley, Jr. et al. | |
| 6,398,795 B1 | 6/2002 | McAlister et al. | |
| 6,416,535 B1 | 7/2002 | Lazarus | |
| 6,423,087 B1 | 7/2002 | Sawada | |
| 6,432,040 B1 | 8/2002 | Meah | |
| 6,447,533 B1 | 9/2002 | Adams | |
| 6,460,543 B1 | 10/2002 | Forsell | |
| 6,475,136 B1 | 11/2002 | Forsell | |
| 6,491,707 B2 | 12/2002 | Makower et al. | |
| 6,494,888 B1 | 12/2002 | Laufer et al. | |
| 6,506,196 B1 | 1/2003 | Laufer | |
| 6,535,764 B2 | 3/2003 | Imran et al. | |
| 6,540,789 B1 | 4/2003 | Silverman et al. | |
| 6,551,310 B1 | 4/2003 | Ganz et al. | |
| 6,554,844 B2 | 4/2003 | Lee et al. | |
| 6,558,400 B2 | 5/2003 | Deem et al. | |
| 6,561,969 B2 | 5/2003 | Frazier et al. | |
| 6,572,629 B2 | 6/2003 | Kalloo et al. | |
| 6,579,301 B1 | 6/2003 | Bales et al. | |
| 6,592,596 B1 | 7/2003 | Geitz | |
| 6,605,037 B1 | 8/2003 | Moll et al. | |
| 6,626,899 B2 | 9/2003 | Houser et al. | |
| 6,632,227 B2 | 10/2003 | Adams | |
| 6,656,194 B1 | 12/2003 | Gannoe et al. | |
| 6,663,598 B1 | 12/2003 | Carrillo, Jr. et al. | |
| 6,663,639 B1 | 12/2003 | Laufer et al. | |
| 6,663,640 B2 | 12/2003 | Kortenbach | |
| 6,675,809 B2 | 1/2004 | Stack et al. | |
| 6,682,520 B2 | 1/2004 | Ingenito | |
| 6,689,062 B1 | 2/2004 | Mesallum | |
| 6,692,485 B1 | 2/2004 | Brock et al. | |
| 6,716,222 B2 | 4/2004 | McAlister et al. | |
| 6,733,512 B2 | 5/2004 | McGhan | |
| 6,736,822 B2 | 5/2004 | McClellan et al. | |
| 6,740,098 B2 | 5/2004 | Abrams et al. | |
| 6,740,121 B2 | 5/2004 | Geitz | |
| 6,746,460 B2 | 6/2004 | Gannoe et al. | |
| 6,746,489 B2 | 6/2004 | Dua et al. | |
| 6,754,536 B2 | 6/2004 | Swoyer et al. | |
| 6,755,849 B1 | 6/2004 | Gowda et al. | |
| 6,755,869 B2 | 6/2004 | Geitz | |
| 6,756,364 B2 | 6/2004 | Barbier et al. | |
| 6,764,518 B2 | 7/2004 | Godin | |
| 6,773,440 B2 | 8/2004 | Gannoe et al. | |
| 6,773,441 B1 | 8/2004 | Laufer et al. | |
| 6,786,898 B2 | 9/2004 | Guenst | |
| 6,790,214 B2 | 9/2004 | Kraemer et al. | |
| 6,802,868 B2 | 10/2004 | Silverman et al. | |
| 6,821,285 B2 | 11/2004 | Laufer et al. | |
| 6,830,546 B1 | 12/2004 | Chin et al. | |
| 6,835,199 B2 | 12/2004 | McGuckin, Jr. et al. | |
| 6,835,200 B2 | 12/2004 | Laufer et al. | |
| 6,837,848 B2 | 1/2005 | Bonner et al. | |
| 6,840,423 B2 | 1/2005 | Adams et al. | |
| 6,845,776 B2 | 1/2005 | Stack et al. | |
| 6,896,682 B1 | 5/2005 | McClellan et al. | |
| 6,916,332 B2 | 7/2005 | Adams | |
| 6,926,722 B2 | 8/2005 | Geitz | |
| 6,966,919 B2 | 11/2005 | Sixto, Jr. et al. | |
| 6,981,978 B2 | 1/2006 | Gannoe | |
| 6,991,643 B2 | 1/2006 | Saadat | |
| 6,994,715 B2 | 2/2006 | Gannoe et al. | |
| 7,020,531 B1 | 3/2006 | Colliou et al. | |
| 7,025,791 B2 | 4/2006 | Levine et al. | |
| 7,033,373 B2 | 4/2006 | de la Torre et al. | |
| 7,033,378 B2 | 4/2006 | Smith et al. | |
| 7,033,384 B2 | 4/2006 | Gannoe et al. | |
| 7,037,343 B2 | 5/2006 | Imran | |
| 7,037,344 B2 | 5/2006 | Kagan et al. | |
| 7,060,078 B2 | 6/2006 | Hathaway et al. | |
| 7,063,715 B2 | 6/2006 | Onuki et al. | |
| 7,083,629 B2 | 8/2006 | Weller et al. | |
| 7,083,630 B2 | 8/2006 | DeVries et al. | |
| 7,087,011 B2 | 8/2006 | Cabiri et al. | |
| 7,097,650 B2 | 8/2006 | Weller et al. | |
| 7,141,055 B2 | 11/2006 | Abrams et al. | |
| 7,220,237 B2 | 5/2007 | Gannoe et al. | |
| 7,229,428 B2 | 6/2007 | Gannoe et al. | |
| 7,235,089 B1 | 6/2007 | McGuckin, Jr. | |
| 7,789,848 B2 | 9/2010 | Gannoe et al. | |
| 2001/0014800 A1 | 8/2001 | Frazier et al. | |
| 2001/0020190 A1 | 9/2001 | Taylor | |
| 2001/0037127 A1 | 11/2001 | De Hoyos Garza | |
| 2002/0022851 A1 | 2/2002 | Kalloo et al. | |
| 2002/0035361 A1 | 3/2002 | Houser et al. | |
| 2002/0040226 A1 | 4/2002 | Laufer et al. | |
| 2002/0047036 A1 | 4/2002 | Sullivan et al. | |
| 2002/0058967 A1 | 5/2002 | Jervis | |

| | | |
|---|---|---|
| 2002/0072761 A1 | 6/2002 | Abrams et al. |
| 2002/0077661 A1 | 6/2002 | Saadat |
| 2002/0078967 A1 | 6/2002 | Sixto, Jr. et al. |
| 2002/0082621 A1 | 6/2002 | Schurr et al. |
| 2002/0143346 A1 | 10/2002 | McGuckin, Jr. et al. |
| 2002/0165589 A1 | 11/2002 | Imran et al. |
| 2002/0183768 A1 | 12/2002 | Deem et al. |
| 2002/0193816 A1 | 12/2002 | Laufer et al. |
| 2003/0040804 A1 | 2/2003 | Stack et al. |
| 2003/0040808 A1 | 2/2003 | Stack et al. |
| 2003/0065340 A1 | 4/2003 | Geitz |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0120285 A1 | 6/2003 | Kortenbach |
| 2003/0120289 A1 | 6/2003 | McGuckin, Jr. et al. |
| 2003/0132267 A1 | 7/2003 | Adams et al. |
| 2003/0158563 A1 | 8/2003 | McClellan et al. |
| 2003/0158601 A1 | 8/2003 | Silverman et al. |
| 2003/0171760 A1 | 9/2003 | Gambale |
| 2003/0208209 A1 | 11/2003 | Gambale et al. |
| 2003/0216754 A1 | 11/2003 | Kraemer et al. |
| 2003/0225312 A1 | 12/2003 | Suzuki et al. |
| 2004/0006351 A1 | 1/2004 | Gannoe et al. |
| 2004/0009224 A1 | 1/2004 | Miller |
| 2004/0010271 A1 | 1/2004 | Kortenbach |
| 2004/0024386 A1 | 2/2004 | Deem et al. |
| 2004/0037865 A1 | 2/2004 | Miller |
| 2004/0039452 A1 | 2/2004 | Bessler |
| 2004/0044354 A1 | 3/2004 | Gannoe et al. |
| 2004/0049209 A1 | 3/2004 | Benchetrit |
| 2004/0059349 A1 | 3/2004 | Sixto, Jr. et al. |
| 2004/0059354 A1 | 3/2004 | Smith et al. |
| 2004/0059358 A1 | 3/2004 | Kortenbach et al. |
| 2004/0082963 A1 | 4/2004 | Gannoe et al. |
| 2004/0087885 A1* | 5/2004 | Kawano et al. .................. 604/8 |
| 2004/0087977 A1 | 5/2004 | Nolan et al. |
| 2004/0088008 A1 | 5/2004 | Gannoe et al. |
| 2004/0089313 A1 | 5/2004 | Utley et al. |
| 2004/0092892 A1 | 5/2004 | Kagan et al. |
| 2004/0092974 A1 | 5/2004 | Gannoe et al. |
| 2004/0097989 A1 | 5/2004 | Molina Trigueros |
| 2004/0107004 A1 | 6/2004 | Levine et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133147 A1 | 7/2004 | Woo |
| 2004/0133238 A1 | 7/2004 | Cerier |
| 2004/0138525 A1 | 7/2004 | Saadat |
| 2004/0138526 A1 | 7/2004 | Guenst |
| 2004/0138529 A1 | 7/2004 | Wiltshire et al. |
| 2004/0138531 A1 | 7/2004 | Bonner et al. |
| 2004/0138682 A1 | 7/2004 | Onuki et al. |
| 2004/0147958 A1 | 7/2004 | Lam et al. |
| 2004/0148021 A1 | 7/2004 | Cartledge et al. |
| 2004/0148034 A1 | 7/2004 | Kagan et al. |
| 2004/0158331 A1 | 8/2004 | Stack et al. |
| 2004/0162568 A1 | 8/2004 | Saadat |
| 2004/0167546 A1 | 8/2004 | Saadat et al. |
| 2004/0172141 A1 | 9/2004 | Stack et al. |
| 2004/0181242 A1 | 9/2004 | Stack et al. |
| 2004/0193190 A1 | 9/2004 | Liddicoat et al. |
| 2004/0210243 A1 | 10/2004 | Gannoe et al. |
| 2004/0215180 A1 | 10/2004 | Starkebaum et al. |
| 2004/0220516 A1 | 11/2004 | Solomon et al. |
| 2004/0225183 A1 | 11/2004 | Michlitsch et al. |
| 2004/0225194 A1 | 11/2004 | Smith et al. |
| 2004/0225305 A1 | 11/2004 | Ewers et al. |
| 2004/0236357 A1 | 11/2004 | Kraemer et al. |
| 2004/0249362 A1 | 12/2004 | Levine et al. |
| 2005/0010162 A1 | 1/2005 | Utley et al. |
| 2005/0033328 A1 | 2/2005 | Laufer et al. |
| 2005/0038415 A1 | 2/2005 | Rohr et al. |
| 2005/0049614 A1 | 3/2005 | Cendan |
| 2005/0049718 A1 | 3/2005 | Dann et al. |
| 2005/0055038 A1 | 3/2005 | Kelleher et al. |
| 2005/0055039 A1 | 3/2005 | Burnett et al. |
| 2005/0075622 A1 | 4/2005 | Levine et al. |
| 2005/0075653 A1 | 4/2005 | Saadat et al. |
| 2005/0080438 A1 | 4/2005 | Weller et al. |
| 2005/0080444 A1 | 4/2005 | Kraemer et al. |
| 2005/0085787 A1 | 4/2005 | Laufer |
| 2005/0096750 A1 | 5/2005 | Kagan et al. |
| 2005/0119671 A1 | 6/2005 | Reydel et al. |
| 2005/0119674 A1 | 6/2005 | Gingras |
| 2005/0143760 A1 | 6/2005 | Imran |
| 2005/0148818 A1 | 7/2005 | Mesallum |
| 2005/0149067 A1 | 7/2005 | Takemoto et al. |
| 2005/0149114 A1 | 7/2005 | Cartledge et al. |
| 2005/0177176 A1 | 8/2005 | Gerbi et al. |
| 2005/0192599 A1 | 9/2005 | Demarais |
| 2005/0192601 A1 | 9/2005 | Demarais |
| 2005/0194038 A1 | 9/2005 | Brabec et al. |
| 2005/0194294 A1 | 9/2005 | Oexle et al. |
| 2005/0194312 A1 | 9/2005 | Niemeyer et al. |
| 2005/0195925 A1 | 9/2005 | Traber |
| 2005/0195944 A1 | 9/2005 | Bartels et al. |
| 2005/0196356 A1 | 9/2005 | Leinen et al. |
| 2005/0197540 A1 | 9/2005 | Liedtke |
| 2005/0197622 A1 | 9/2005 | Blumenthal et al. |
| 2005/0197684 A1 | 9/2005 | Koch |
| 2005/0198476 A1 | 9/2005 | Gazsi et al. |
| 2005/0203547 A1 | 9/2005 | Weller et al. |
| 2005/0203548 A1 | 9/2005 | Weller et al. |
| 2005/0228415 A1 | 10/2005 | Gertner |
| 2005/0228504 A1 | 10/2005 | Demarais |
| 2005/0256533 A1 | 11/2005 | Roth et al. |
| 2005/0256587 A1* | 11/2005 | Egan .......................... 623/23.65 |
| 2006/0020247 A1 | 1/2006 | Kagan et al. |
| 2006/0020254 A1 | 1/2006 | Hoffmann |
| 2006/0020276 A1 | 1/2006 | Saadat et al. |
| 2006/0036267 A1 | 2/2006 | Saadat et al. |
| 2006/0106288 A1 | 5/2006 | Roth et al. |
| 2006/0111735 A1 | 5/2006 | Crainich |
| 2006/0122462 A1 | 6/2006 | Roth et al. |
| 2006/0142787 A1 | 6/2006 | Weller et al. |
| 2006/0151568 A1 | 7/2006 | Weller et al. |

FOREIGN PATENT DOCUMENTS

| | | |
|---|---|---|
| EP | 0 174 843 A2 | 3/1986 |
| EP | 0 246 999 A1 | 11/1987 |
| EP | 0 540 010 A2 | 5/1993 |
| JP | 63277063 A | 11/1988 |
| JP | 63279854 A | 11/1988 |
| JP | 63302863 A | 12/1988 |
| JP | 1049572 A | 2/1989 |
| JP | 4297219 A | 10/1992 |
| WO | WO-94/18893 A1 | 9/1994 |
| WO | WO-99/17662 A1 | 4/1999 |
| WO | WO-99/53827 A1 | 10/1999 |
| WO | WO-00/32137 A1 | 6/2000 |
| WO | WO 00/39708 A1 | 7/2000 |
| WO | WO-00/48656 A1 | 8/2000 |
| WO | WO-00/78227 A1 | 12/2000 |
| WO | WO-00/78229 A1 | 12/2000 |
| WO | WO-01/66018 A1 | 9/2001 |
| WO | WO-01/67964 A2 | 9/2001 |
| WO | WO-01/85034 A1 | 11/2001 |
| WO | WO-0224080 A2 | 3/2002 |
| WO | WO-0235980 A2 | 5/2002 |
| WO | WO-0239880 A2 | 5/2002 |
| WO | WO 02/071951 A1 | 9/2002 |
| WO | WO 02/091961 A1 | 11/2002 |
| WO | WO 02/096327 A2 | 12/2002 |
| WO | WO 03/007796 A2 | 1/2003 |
| WO | WO 03/017882 A2 | 3/2003 |
| WO | WO 03/078721 A2 | 9/2003 |
| WO | WO-03086247 A1 | 10/2003 |
| WO | WO-03088844 A1 | 10/2003 |
| WO | WO-03094785 A1 | 11/2003 |
| WO | WO-03099140 A1 | 12/2003 |
| WO | WO-03105563 A2 | 12/2003 |
| WO | WO-03105671 A2 | 12/2003 |
| WO | WO-2004/009269 A2 | 1/2004 |

| | | |
|---|---|---|
| WO | WO-2004/014237 A1 | 2/2004 |
| WO | WO-2004/017863 A2 | 3/2004 |
| WO | WO-2004/019787 A2 | 3/2004 |
| WO | WO-2004/019826 A1 | 3/2004 |
| WO | WO-2004/037064 A2 | 5/2004 |
| WO | WO-2004/049911 A2 | 6/2004 |
| WO | WO-2004/058102 A2 | 7/2004 |
| WO | WO-2004/060150 A1 | 7/2004 |
| WO | WO-2004/087014 A2 | 10/2004 |
| WO | WO-2004/103189 A1 | 12/2004 |
| WO | WO-2005/023118 A1 | 3/2005 |
| WO | WO-2005037152 A1 | 4/2005 |
| WO | WO-2005058239 | 6/2005 |
| WO | WO-2005/060882 A1 | 7/2005 |
| WO | WO-2006/078781 A1 | 7/2006 |

OTHER PUBLICATIONS

Benjamin, S.B., *Small Bowel Obstruction and the Garren-Edwards Bubble, Lessons to be Learned?* Abstracts, Submitted to AIS/G/E 1987, Division of Gastroenterology, Department of Medicine, Georgetown University Hospital, Washington, D.C.

Boyle, Thomas M., M.D., et al., *Small Intestinal Obstruction Secondary to Obturation bya Garren Gastric Bubble*, The American Journal of Gastroenterolol!v, vol. 82, No. I, PII. 51-53, 1987.

Buchler, M.W., M.D. et a!., *A Technique for Gastroplasty As A Substitute For The Esophagus: Fundus Rotation Gastroplasty*, Journal Of The American College Of Surgeons, vol. 182, pp. 241-245, Mar. 1996.

Cass, O.W., et a!., *Long-Term Follow-Up of Patients With Percutaneous Endoscopic Gastrostomy (PEG)*, Abstracts, Submitted to AIS/G/E 1987, Department of Medicine, Hennepin County Medical Center, Minneapolis, MN 55415.

Chang, Craig G. M.D. ',et al.. *Gastro-Clip® Gastroplasty: A Very Long-Term Complication*, Obesity Surgery, 14, © FD-Communications Inc. 2004.

Clark, Charlene, R.N., *The Gastric Bubble: Medicine. Magic or Mania?* SGA Journal, vol. 9, No. 2, pp. 45-47, Fall 1986.

Cummings, David E., M.D., et al., *Plasma Ghrelin Levels After Diet-induced Weight Loss or Gastric Bypass Surgery*, New England Journal of Medicine vol. 346, No. 21, pp. 1623-1630, May 23, 2002.

Davenport, Horace W., Ph.D., D.Sc., Physiology of the Digestive Tract: An Introductory Text, 3d Ed., Cover and Table of Contents.

DeMeester, Tom T., M.D., *Evolving Concepts of Reflux: The Ups and Downs of the LES*, Canadian Journal of Gastroenterolollv, vol. 16, No. 5, pp. 327-331, 2002.

De Waele, 8., M.D., et al., *in/ragastric Balloons for Preoperative Weight Reduction*, Obesity Surgery. vol. 10, pp. 58-60,2000.

Edell, Steven L., et al., *Radiographic Evaluation of the Garren Gastric Bubble*, American Journal of Radiology, vol. 145, pp. 49-50, Jul. 1985.

Endo Gia• Universal, Single Use Stapler and Endo GIA Roticulator•, Brochure, 8 pages, Undated.

Filipi, Charles J. M.D., et al., Transoral, *Flexible Endoscopic Suturing For Treatment Of GERD: A Multicenter Trial*, Gastrointestinal EndoscoDV,. vol. 53, No. 4, pp. 416-422, 2001.

Gray, Henry, R.R.s., Anatomy of the Human Body. *The Digestive System*, Thirtieth American Edition, pp. 1466-1467 (Undated).

Guidant, Internet, AXIUSTM VACUUM 2 Stabilizer Systems, Internet Website—www.guidanL comlproducts/axius vacuum.shtml, 8 pages, visited May 27, 2003.

Gukovsky-Reicher, S., M.D. et al., *Expandable Metal Esophageal Stents: Efficacy and Safety. Review of Current Literature Data and of 53 Stents Placed at Harbor-UCLA Medical Center*, www.medscape.comlviewarticlel423508 print pp. 1-20, Medscape General Medicine 4(1), 2003 ~2002 Medscape, downloaded Oct. 9, 2006.

Hepworth, Clive C. FRCS et al., *Mechanical Endoscopic Methods of Haemostasis for Bleeding Peptic Ulcers: A Review*, Bailliere's Clinical Gastroenterology. vol. 14, No. 3 pp. 467-476, 2000.

Ikeda, Y. et al., *New Suturing Device for Transanal Endoscopic Microsurgery*, Blackwell Science Ltd. p. 1290, 1997.

Johnson & Johnson Gateway"" Endopath 3mm, 5mm and 10 mm Diameter Endoscopic Instruments. Internet Website—www.inigateway.com/home.ihtml?loc=USENG&page-viewContent &parentld-0900 . . . , 3 pages., visited May 29, 2003.

Kirby, Donald F., *Incomplete Small Bowel Obstruction by the Garren-Edwards Gastric Bubble Necessitating Surgical Intervention*, The American Journal of Gastroenterology, vol. 82, No. 3, pp. 251-253, 1987.

Nieben, Ole Gyring, et al., *Intragastric Balloon as an Artificial Bezoar for Treatment of Obesity*, The Lancet, pp. 198-199, Jan. 23,1982.

Percival, Walter L., M.D., *"The Balloon Diet"; A Noninvasive Treatment for Morbid Obesity. Preliminary Report of 1908 Patients*, The Canadian Journal of Surgery, vol. 21, No. 2, pp. 135-136.

Power Medical Interventions Digital and Wireless Medical Technology, Product Innovation: SurgASSISTTM, Internet Website—www/pmi2.comlaccess flexibility. asp, 6 pages, visited May 29, 2003.

Snowden Pencer, Diamon-Flex Angled Snake Retractor (class 1, 878.4800), Appendix F.f, Undated.

Stoltenberg, P.N., et al., *Intragastric Balloon Therapy of Obesity: A Randomized Double-Blind Trial*, Abstracts of Papers 1985, Scott & White Clinic, Texas A&M College of Medicine, Temple, Texas.

Swain, C. Paul, M.D. et al., *An Endoscopic Sewing Machine*, Gastrointestinal Edoscopy, vol. 32, No. I pp. 36-38 1986.

Swain, C. Paul, M,D *Endoscopic Sewing and Stapling Machines*, Endoscopy pp. 205-210, © Georg Thieme Verlag Stuttgart, New York, 1997.

Swain, C. Paul, M,D. et al., *An Endoscopic Stapling Device: The Development OJ A New Flexible Endoscopically Controlled Device For Placing Multiple Transmural Staples In Gastrointestinal Tissue*, Gastrointestinal Endoscopy, vol. 35, No. 4, pp. 338-339, 1989.

Swain, C. Paul, M.D., *Endoscopic Suturing*. Bailliere's Clinical Gastroenterology, Bailliere's Tindall vol. J 3 No. I, pp. 97-108, 1999.

Taylor, T. Vincent, et al., *Gastric Balloons for Obesity*, The Lancet, Abstract, Mar. 27, 1982.

Vandenplas, Y., et al., *Intragastric Balloons in Adolescents With Morbid Obesity*, European Journal of Gastroenterology & Hepatology. vol. II, No. 3, pp, 243-245, 1999.

Villar, Hugo V., M,D., et al., *Mechanisms of Satiety and Gastric Emptying After Gastric Partitioning and Bypass*, Surgery, pp, 229-236, Aug. 1981.

Wullstein, C., et al., *Compression Anastomosis (AKA-2) in Colorectal Surgery: Results in 442 Consecutive Patients*, British Journal of Surgery 2000, pp. 1071-1075.

\* cited by examiner

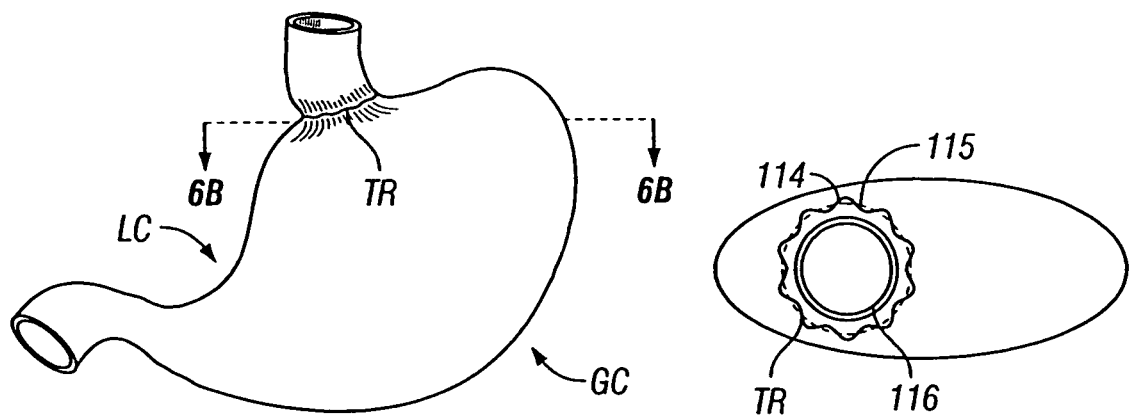
FIG. 6A
FIG. 6B
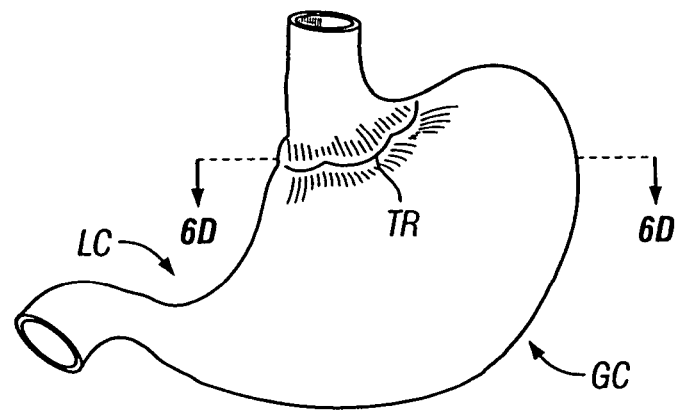
FIG. 6C
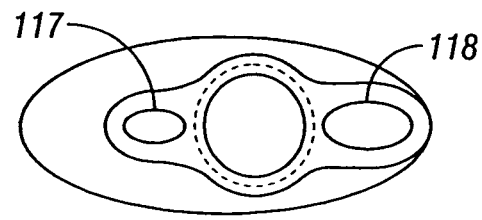
FIG. 6D

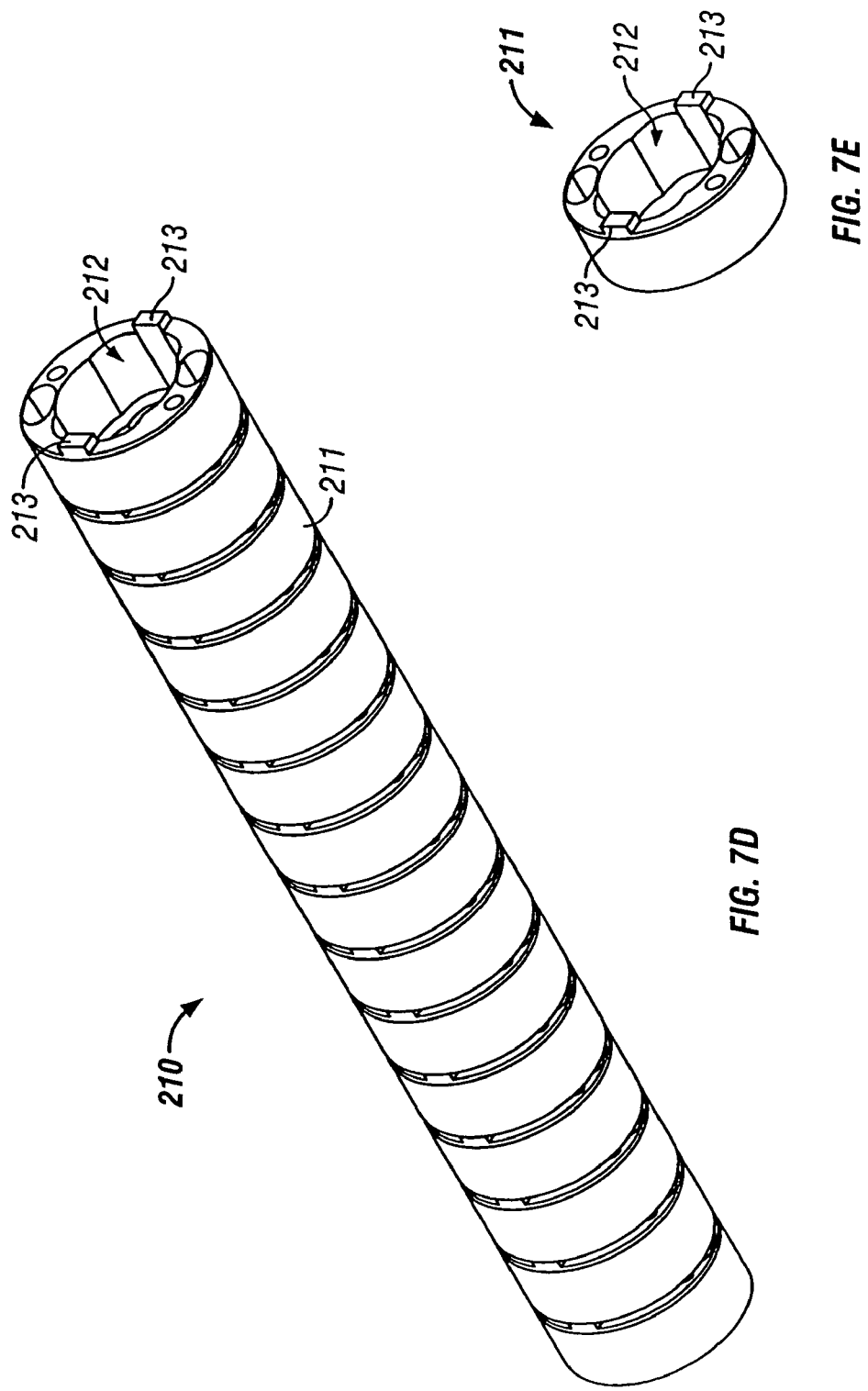

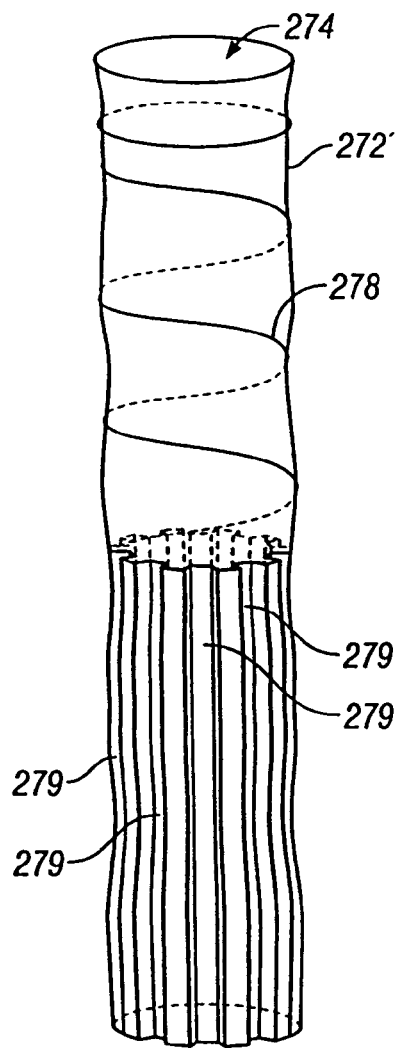 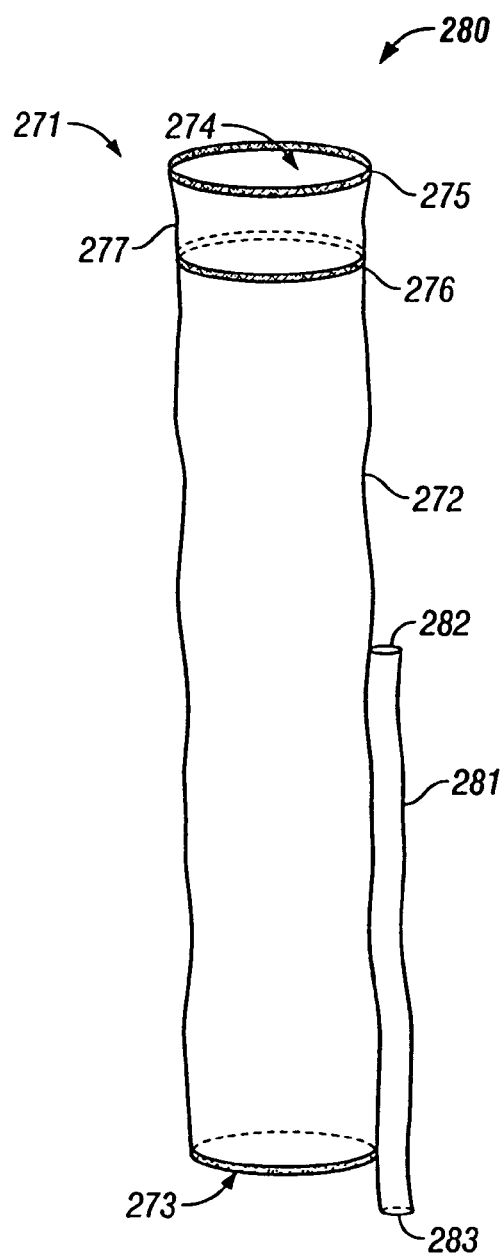
*FIG. 11F*  *FIG. 12*

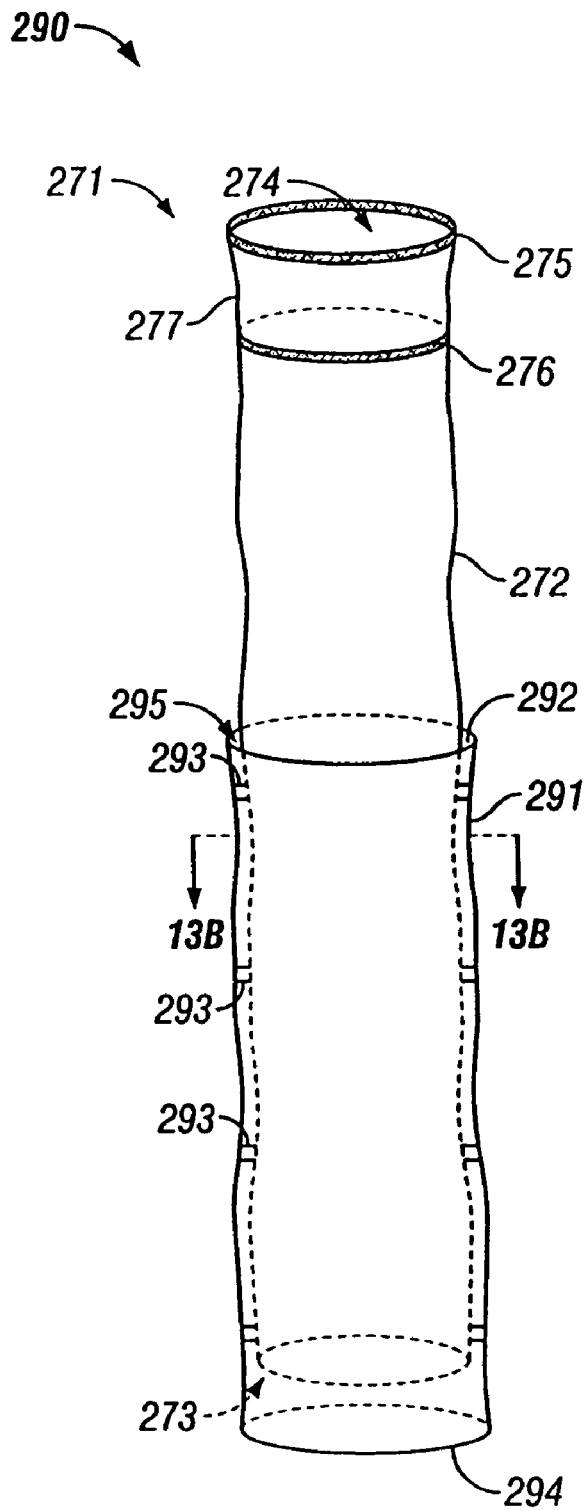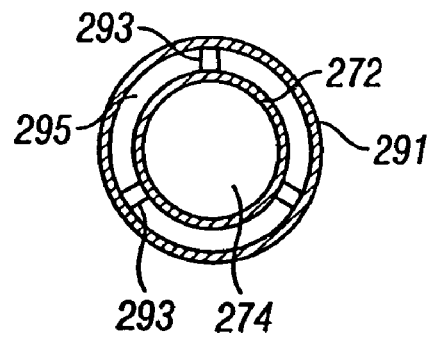
FIG. 13A
FIG. 13B

METHOD AND DEVICE FOR USE IN ENDOSCOPIC ORGAN PROCEDURES

CROSS-REFERENCE TO RELATED APPLICATIONS

This application is a continuation of U.S. Ser. No. 10/351,231 filed Jan. 24, 2003 now U.S. Pat. No. 7,220,237, which is a continuation-in-part of U.S. patent application Ser. No. 10/279,257 filed Oct. 23, 2002 now U.S. Pat. No. 7,229,428, both of which are incorporated herein by reference in their entirety.

FIELD OF THE INVENTION

The present invention relates generally to medical apparatus and methods and more particularly to devices and methods for dividing a hollow body organ or otherwise restricting or partitioning a certain section of that organ, such as a stomach, intestine or gastrointestinal tract as well as devices and methods for placing a liner within or partially within the hollow body organ.

BACKGROUND OF THE INVENTION

In cases of severe obesity, patients may currently undergo several types of surgery either to tie off or staple portions of the large or small intestine or stomach, and/or to bypass portions of the same to reduce the amount of food desired by the patient, and the amount absorbed by the gastrointestinal tract. The procedures currently available include laparoscopic banding, where a device is used to "tie off" or constrict a portion of the stomach, vertical banded gastroplasty (VBG), or a more invasive surgical procedure known as a Roux-En-Y gastric bypass to effect permanent surgical reduction of the stomach's volume and subsequent bypass of the intestine.

Typically, these stomach reduction procedures are performed surgically through an open incision and staples or sutures are applied externally to the stomach or hollow body organ. Such procedures can also be performed laparoscopically, through the use of smaller incisions, or ports, through trocars and other specialized devices. In the case of laparoscopic banding, an adjustable band is placed around the proximal section of the stomach reaching from the lesser curve (LC) of the stomach around to the greater curve (GC), thereby creating a constriction or "waist" in a vertical manner between the esophagus (ES) and the pylorus (PY) (See Prior Art FIG. 1). During a VBG (See Prior Art FIG. 2) a small pouch (P) (approximately 20 cc in volume) is constructed by forming a vertical partition from the gastroesophageal junction (GEJ) to midway down the lesser curvature of the stomach by externally applying staples, and optionally dividing or resecting a portion of the stomach, followed by creation of a stoma (ST) at the outlet of the partition to prevent dilation of the outlet channel and restrict intake. In a Roux-En-Y gastric bypass (see Prior Art FIG. 3), the stomach is surgically divided into a smaller upper pouch connected to the esophageal inflow, and a lower portion, detached from the upper pouch but still connected to the intestinal tract for purposes of secreting digestive juices. A resected portion of the small intestine is then anastomosed using an end-to-side anastomosis to the upper pouch, thereby bypassing the majority of the intestine and reducing absorption of caloric intake and causing rapid "dumping" of highly caloric or "junk foods".

Although the outcome of these stomach reduction surgeries leads to patient weight loss because patients are physically forced to eat less due to the reduced size of their stomach, several limitations exist due to the invasiveness of the procedures, including time, general anesthesia, healing of the incisions and other complications attendant to major surgery. In addition, these procedures are only available to a small segment of the obese population (morbid obesity, Body Mass Index≧40) due to their complications, leaving patients who are considered obese or moderately obese with few, if any, interventional options.

In addition to surgical procedures, certain tools exist for approximating or otherwise securing tissue such as the stapling devices used in the above-described surgical procedures and others such as in the treatment of gastroesophogeal reflux (GERD). These devices include the GIA® device (Gastrointestinal Anastomosis device manufactured by Ethicon Endosurgery, Inc. and a similar product by USSC), and certain clamping and stapling devices as described in U.S. Pat. Nos. 5,897,562 and 5,571,116 and 5,676,674, Non-Invasive Apparatus for Treatment of Gastroesophageal Reflux Disease (Bolanos, et al) and U.S. Pat. No. 5,403,326 Method for Performing a Gastric Wrap of the Esophagus for Use in the Treatment of Esophageal Reflux (Harrison et al) for methods and devices for fundoplication of the stomach to the esophagus for treatment of gastro esophageal reflux (GERD). In addition, certain tools as described in U.S. Pat. No. 5,947,983 Tissue Cutting and Stitching Device and Method (Solar et al), detail an endoscopic suturing device (C.R.Bard, Inc., Billerica, Mass.) that is inserted through an endoscope and placed at the site where the esophagus and the stomach meet. Vacuum is then applied to acquire the adjacent tissue, and a series of stitches are placed to create a pleat in the sphincter to reduce the backflow of acid from the stomach up through the esophagus. These devices can also be used transorally for the endoscopic treatment of esophageal varices (dilated blood vessels within the wall of the esophagus).

Further, certain devices are employed to approximate tissue such as in U.S. Pat. No. 5,355,897 (Pietrafitta) describing the use of a circular stapler to perform a pyloroplasty to create a narrowing at the pylorus. In addition, intraluminal anastomosis, such as bowel anastomosis, use suturing or stapling and employ tools such as the circular stapler, such as that described in U.S. Pat. No. 5,309,927 (Welch), U.S. Pat. No. 5,588,579 (Schnut et al), U.S. Pat. No. 5,639,008 (Gallagher et al), U.S. Pat. No. 5,697,943 (Sauer), U.S. Pat. No. 5,839,639 (Sauer), U.S. Pat. No. 5,860,581 (Robertson et al), and U.S. Pat. No. 6,119,913 (Adams et al). Such circular staplers are available from Ethicon Endosurgery, Cincinnati, Ohio (Proximate™ and EndoPath Stealth™ staplers, see www.surgicalstapling.com), Power Medical Interventions, New Hope, Pa. and United States Surgical, a unit of Tyco Healthcare Group LP, Norwalk, Conn.

There is a need for improved devices and procedures. In addition, because of the invasiveness of most of the surgeries used to treat obesity, and the limited success of others, there remains a need for improved devices and methods for more effective, less invasive hollow organ restriction procedures.

SUMMARY OF THE INVENTION

The present invention provides for improved methods and apparatus for the transoral, or endoscopic, restriction of a hollow body organ, such as the creation of a small stomach pouch. For purposes of the present invention, the hollow body organ shall include the entire gastrointestinal tract, including, but not limited to, the esophagus, stomach, portions of or the entire length of the intestinal tract, etc., unless specified otherwise. In the case of the present invention, the surgeon or endoscopist may insert devices as described below through the patient's mouth, down the esophagus and into the stomach or intestine as appropriate. The procedure can be performed entirely from within the patient's stomach or other organ, and does not require any external incision. The end result of the procedure is the formation of a variety of organ divisions or plications that serve as barriers or "partitions" or "pouches" that are substantially sealed off from the majority of the organ cavity. For example, in the case of dividing the stomach, the "pouch" or partitions that are created may seal a small portion of the stomach just below the esophagus to allow only small amounts of food or liquid to be consumed by the patient. This pouch or partition will mimic the section of stomach sealed off from the majority of the organ in a traditional obesity surgery heretofore described; however, it can be formed and secured entirely from inside the stomach endoscopically, obviating the need for a prolonged procedure, external incisions, minimizing the risk of infections, and in some cases, general anesthesia.

The methods and tools of the present invention may also be used in treating GERD in that stomach folds just below the esophagus can be acquired and fastened to create a desired "pleat", thereby effectively extending the length of the esophagus and preventing reflux. Preferably, multiple folds of tissue can be acquired to effect this end. Further, features of the present invention would assist in the longevity of the GE Junction (GEJ)/Esophageal pleat as compared to current devices and techniques as the plication would include a more significant amount of muscular tissue. In addition, the devices and methods of the present invention may be used to revise or repair failures seen in current surgical procedures, such as dilation of the pouch and/or stoma (stomata) formed in a traditional Roux-En-Y gastric bypass, or VBG. In these cases, when the stoma dilates or shifts, the tools of the present invention would be useful to circumferentially gather tissue at the site of dilation to narrow it, thereby making the stoma functional again, or by further reducing the volume of an existing pouch which has dilated.

The devices shown and described herein can be used to form a pouch or partition by the approximation and fixation of a circular section of tissue acquired circumferentially from the walls of the target organ. The tissue acquisition device and fastener may include an acquisition feature (utilizing, e.g., a vacuum, and/or some other mechanical method for acquiring a circumferential "bite" of tissue), a fixation element (such as a stapling mechanism) and possibly a cutting element. In addition, the device may be adapted to receive a standard endoscope to allow viewing of the target region at various points during the procedure. The devices may be articulatable through a variety of conventional methods; alternatively, they may be articulated by a endoscope or other articulation device inserted within.

The fastening assembly of the present invention may employ a similar design and function to those circular staplers heretofore referenced, taking advantage of their ability to deploy multiple rows of staples with one actuation, and their relative clinical efficacy in performing other types of fastening (e.g. anastomoses procedures, hemorrhoid plication, etc.). Such devices can be adapted to perform the novel procedures described herein. Such devices may be adapted to incorporate a tissue acquisition system within the stapler body to allow sufficient tissue to be acquired during a procedure, and other modifications may be done to enable use of the stapler in these novel procedures.

In the procedures of the present invention relating to treatment of gastric disorders such as gastroesophageal reflux disease (GERD), or in cases of treating obesity, a flexible circular stapler may be inserted transorally down the patient's esophagus and into the stomach at the region of the GEJ. Tissue may then be acquired circumferentially about the stapler device, or at least partially about the circumference of the stapler device at some point less than 360 degrees (possibly in a 180 degree formation) relative to a longitudinal axis of the device such that the tissue acquisition creates a "waist" within the organ volume. Subsequently, the tissue fixation element may then be deployed to fix the tissue in a manner to promote healing.

As set forth in U.S. patent application Ser. No. 10/188,547 filed Jul. 2, 2002, which is fully incorporated herein by reference in its entirety, the layered tissue structure of, e.g., the stomach, and the amount of desirable tissue acquisition and approximation is described in further detail. The devices and procedures of the present invention would allow the operator to reliably acquire and secure the necessary type of tissue, such as the muscularis, in creating the circumferential or curved tissue plication desirable to ensure a lasting clinical result.

Any of the fastening devices described herein may employ, e.g., bioabsorbable or biofragmentable staples or fixation element. Such fastening devices would typically dissolve or otherwise degrade leaving only the fixation region once the desired tissue healing has occurred. The remaining healed tissue, now a tissue "ring" (TR), would be sufficiently adhered or healed together to maintain the integrity of the pouch and stoma. In addition, the fastening devices may include coatings or other secondary features to aid healing, such as resorbable meshes, sclerosing agents, surgical felt, or tissue grafts.

The pouch or partitions may be created by a procedure of the present invention to remain permanently within the stomach to restrict it indefinitely. Alternatively, the creation of the pouch or partitions may be reversible (e.g., once weight loss is achieved, or reflux minimized) or revised (in the event pouch side needs to be modified). Reversal can also be achieved via various methods such as dilation of the restricted section, or, e.g., using an electro-surgical device such as a bovine to cut the restricted section to free the tissue folds. Further, if the physician so desires, techniques of the present invention may be augmented or assisted by the use of other techniques such as laparoscopy. Optionally, techniques of the present invention may be combined with other procedures such as for the treatment of GERD or the transoral placement of a bypass prosthesis or other type of liner in the intestine to bypass the hormonally active portion of the small intestine, typically between the stoma to just proximal of the jejunum. Such a liner may be placed within the orifice of a stoma created by devices described herein or within stomas created by various conventional procedures, as also described herein. For present purposes, a stoma refers simply to an artificial or "man made" narrowing within a body organ. The liner may be tubular in construction and made to match the diameter of the stoma created by the present invention such that they can be hooked together to achieve the desired clinical effect. Additionally, the distal end of the liner may also be anchored to tissue distally located from the stoma or it may be left unanchored relying on its resilient physical structure to avoid kinking or twisting.

Moreover, such a liner may vary in construction and in placement within the stomach. The liner, which acts as a bypass conduit, may also include fenestrations or openings that provide for fluid communication between the stomach cavity (for instance, following a bypass procedure the remaining stomach cavity is commonly referred to as the "gastric remnant") and/or common duct (e.g., the duct that enters the intestine at the duodenal ampulla), and certain parts of the intestinal tract to maintain alimentary flow of digestive secretions. Allowing such flow may facilitate in preventing adhesions from forming between the liner and regions of the intestines. Such adhesions may typically cause blockage of the common duct with potentially fatal consequences, such as bowel necrosis. The liner may also include a secondary fluid conduit adjacently positioned along the liner to provide for fluid communication. The fluid conduit may thus have a length which is less than, greater than, or equal to a length of the liner and sufficient to communicate from the inflow point (e.g., gastric remnant or duodenal ampulla) and a point in the lower intestine (e.g., near the jejunum). The liner and fluid conduit may also be configured to ensure that the liner and/or fluid conduit does not inhibit fluid communication from the common bile ducts, such as channels or fenestrations along their length. The fluid conduit may be attached to the liner as a parallel tube or in any number of configurations. Another variation may have the fluid conduit as a coaxial tube positioned about the liner.

In either case, the liner may define one or more fenestrations or channels on the portion of the liner in communication with the gastric remnant, and/or at or near the site of the common bile ducts so as to allow fluids to drain from the organ or ducts. The liner and the fluid conduit may be made separately and attached together or they may be made integrally from the same material. Also, the liner and/or the fluid conduit may be made of a braided design to inhibit kinking as the device reacts to the peristalsis motion of the intestines. Another alternative may utilize a singular liner having one or more channels defined longitudinally along the outer surface of the liner rather than as a separate fluid conduit. These channels may form spaces between the tissue and the liner itself to allow for the flow of fluids within the channels. In another variation of the singular liner, the liner may have fenestrations or openings positioned along its length near or at the zones of active secretion in the intestines to permit fluid flow from the organ or bile ducts into the lumen of the liner (so as to prevent blockage thereof), while still maintaining a barrier to the majority of the intestine to achieve malabsorption and to facilitate "dumping" syndrome upon ingestion of high fat or high caloric foods. An alternative variation of this singular liner may have multiple valved openings along its length to allow for the unidirectional flow of secretions into the liner, but prohibiting contact between the intestines and the food contents within the liner.

BRIEF DESCRIPTION OF THE DRAWINGS

FIGS. 6A-6D shows a schematic depiction of an organ (stomach) following completion of one variation on a procedure of the present invention and the resulting cross sectional view of the treated region in various configurations;

FIGS. 7A-7F show a variation on the circular tissue acquisition and fixation device of the present invention, including details on the inner working elements and flexible shaft thereof;

FIG. 11F depicts a variation of the bypass conduit assembly having an irregular cross section.

FIG. 12 depicts another variation of the bypass conduit assembly but with the addition of a fluid bypass conduit located adjacent the conduit wall.

FIGS. 13A-13B depict perspective and cross-sectional views, respectively, of another variation of the bypass conduit having a coaxial fluid bypass conduit.

DETAILED DESCRIPTION OF THE INVENTION

The present invention provides, in part, for methods and devices for hollow organ division and restriction, more particularly providing methods and devices to perform a transoral, endoscopically mediated stomach reduction for purposes of, e.g., treating obesity. For purposes of the present invention, the hollow body organ shall include the entire gastrointestinal tract, including, but not limited to, the esophagus, stomach, portions of or the entire length of the intestinal tract, etc., unless specified otherwise.

Figure 1:
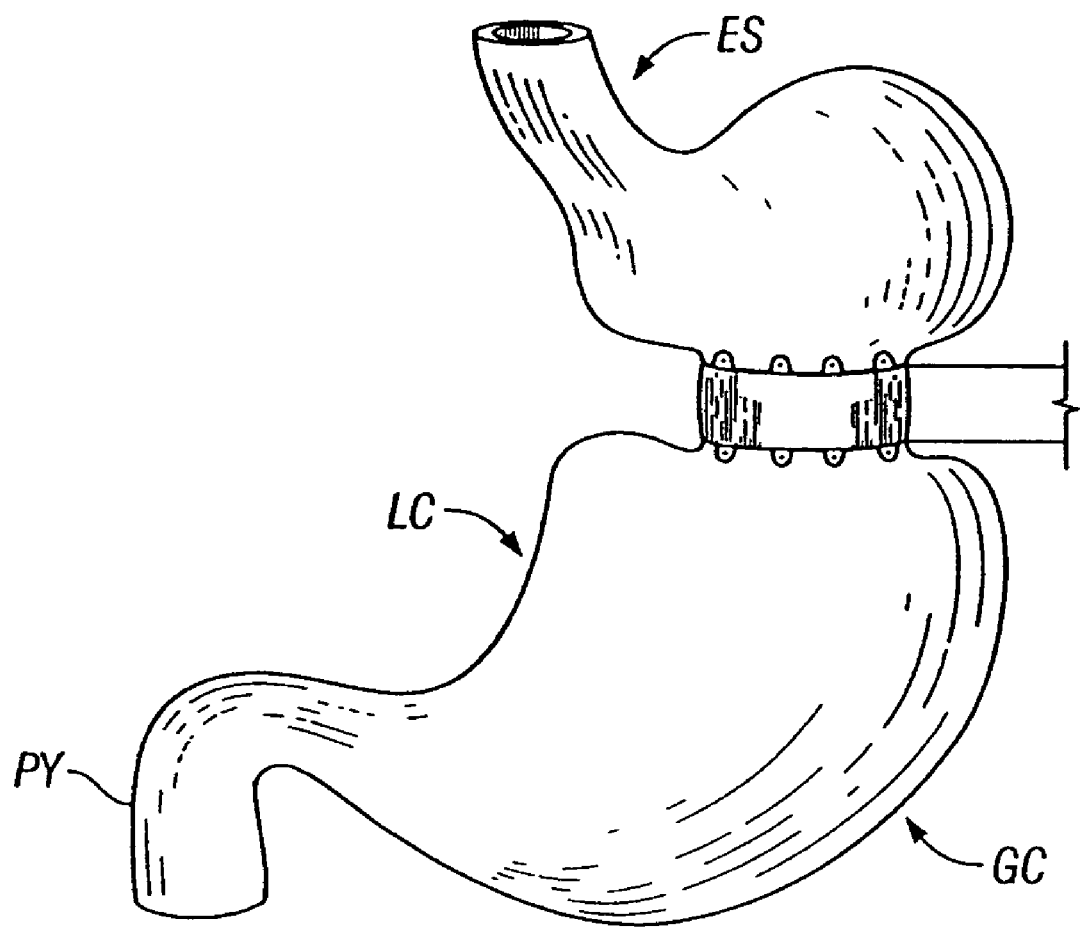
FIG. 1 depicts the prior art procedure commonly known as laparoscopic banding.
Figure 2:
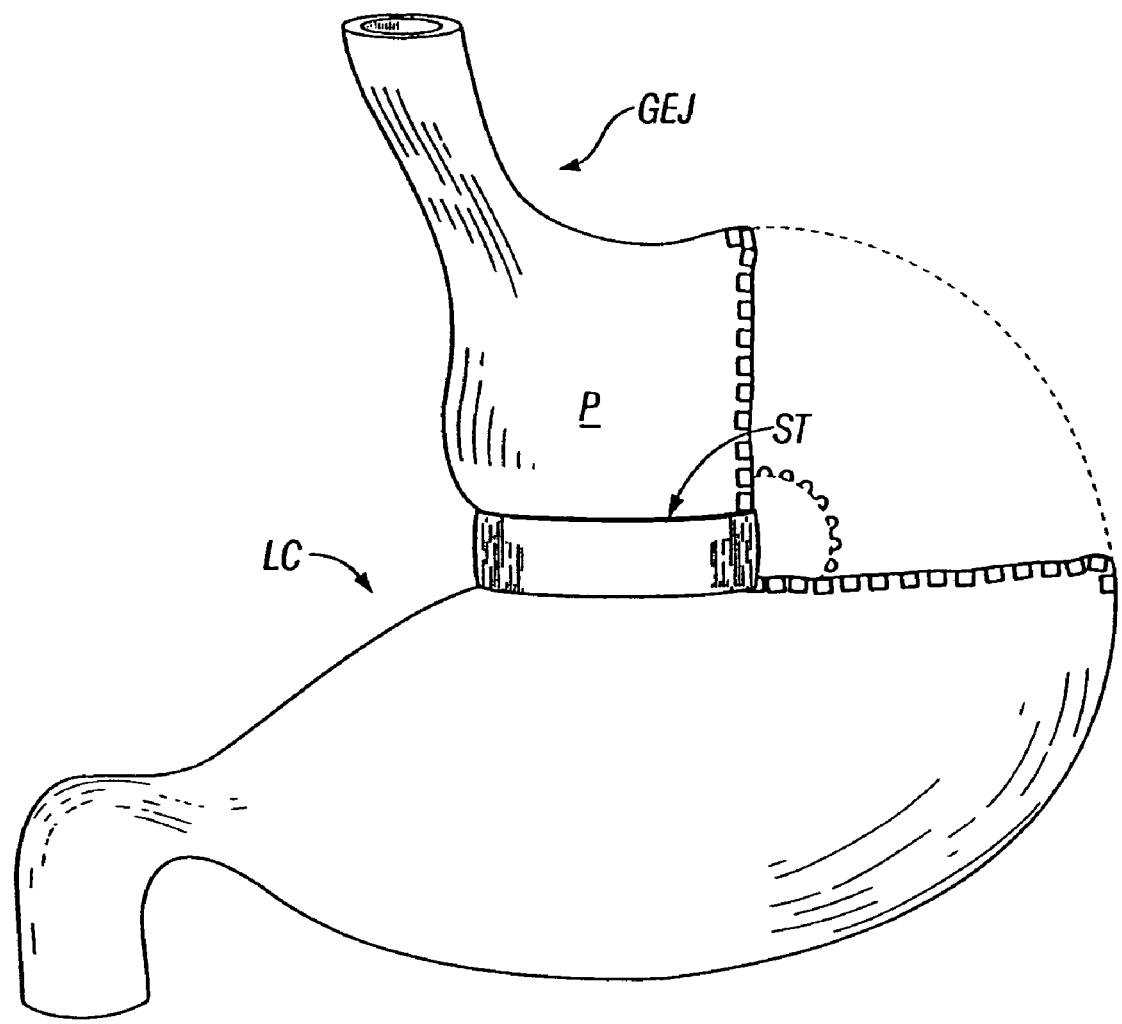
FIG. 2 depicts the prior art procedure commonly known as the vertical banded gastroplasty or "VBG"
Figure 3:
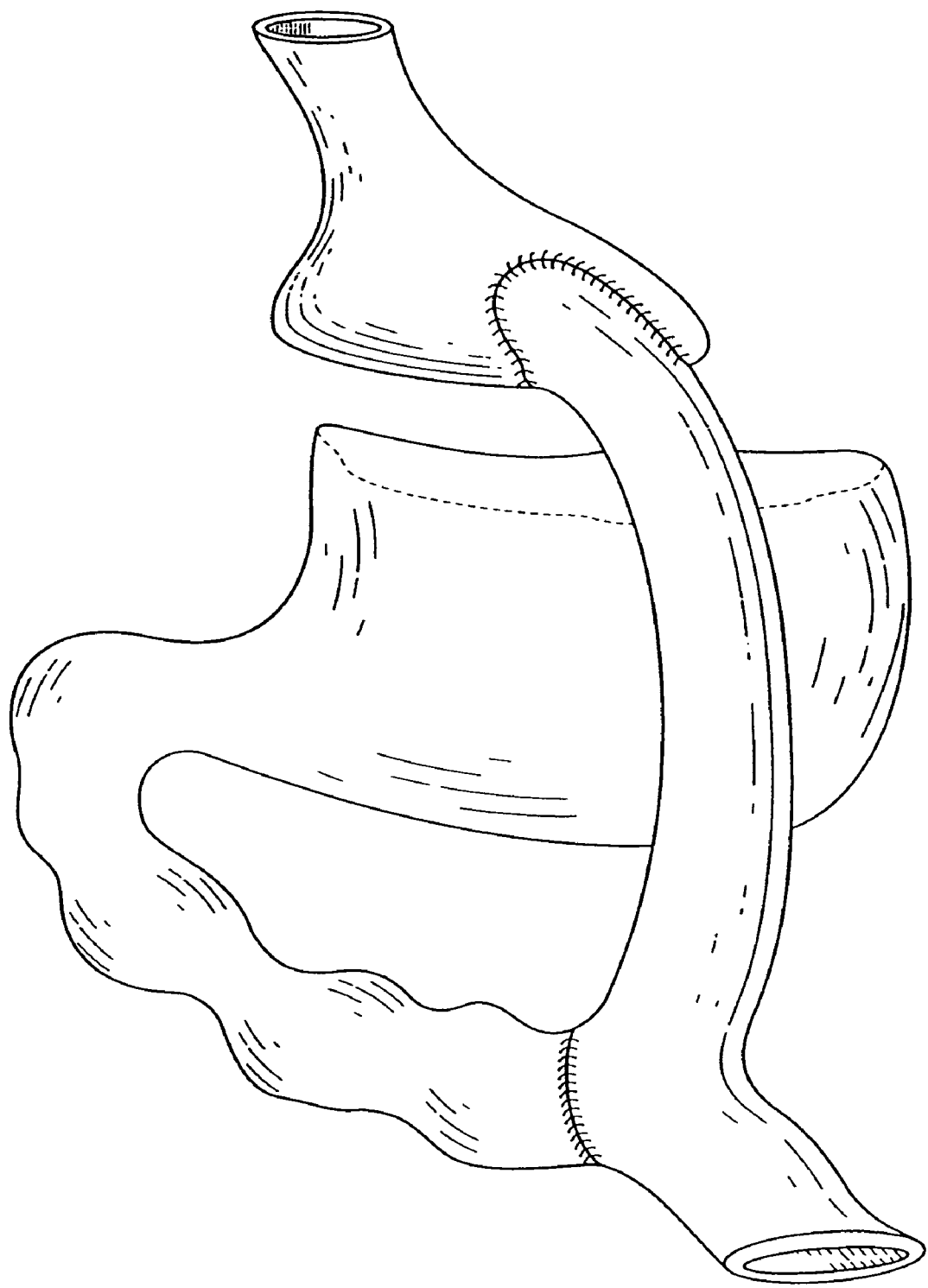
FIG. 3 depicts the prior art procedure commonly know as surgical Roux-En-Y procedure.
Figure 4A:
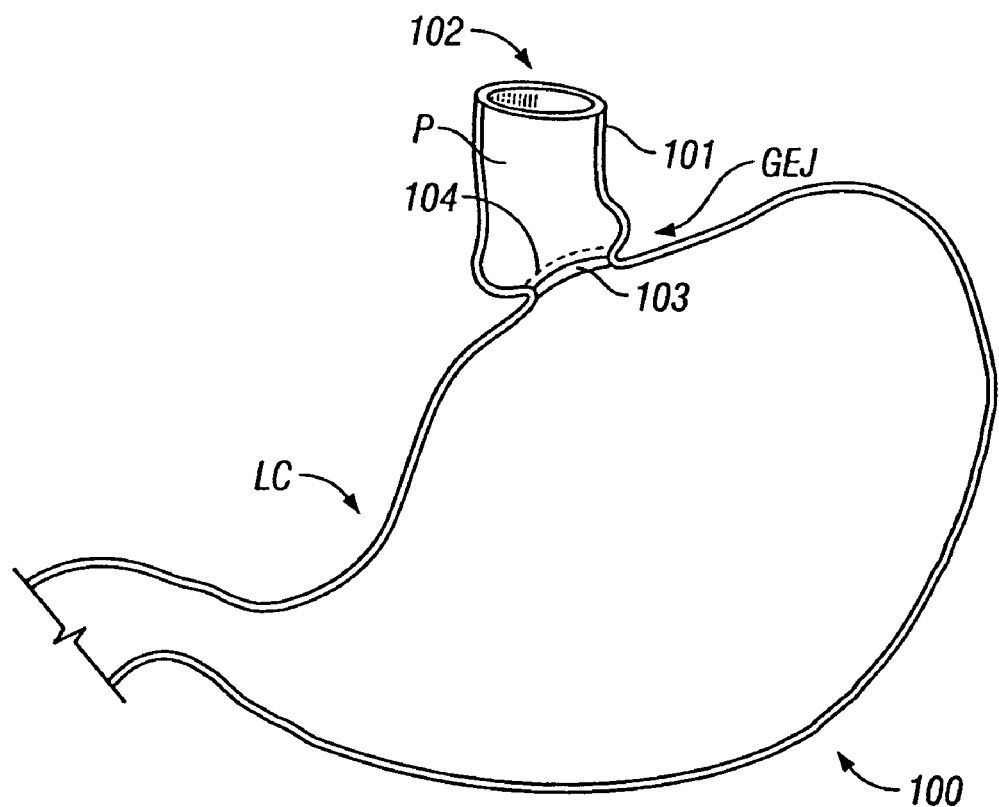
FIG. 4A-4B depicts one variation on a procedure of the present invention, showing a cut-away section of the tissue being acquired by the distal tip of the device of the present invention, and the resulting modification to the body organ (creation of a "pouch" within the stomach)
Figure 4B:
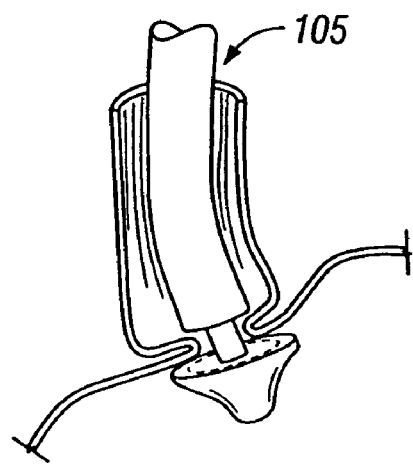

As previously discussed, the results of some clinical procedures of the prior art are shown in FIGS. 1-3, from a perspective external to the stomach. An example of a result of the procedure in one variation of the present invention is shown in FIG. 4A, which depicts an external anterior view of a stomach organ 100, having an esophagus 101 (cut away to reveal the esophageal lumen 102), and further depicting a circumferential orifice or stoma 103, configured from staple line 104, producing a pouch (P). Orifice 103 is preferably positioned close to and on the distal side of the gastroesophageal junction (GEJ) at the base of the esophagus, and angled toward the lesser curve of the stomach (LC), leaving a stoma or opening having a diameter of approximately 1 cm between the pouch (P) and the remaining stomach volume. A desirable pouch (P) volume is between 15-100 cc, preferably 15-20 cc. The orifice 103 operates to restrict food from emptying from the pouch, while still allowing communication between the pouch and the greater stomach volume for purposes of passage of digestive fluids and secretions and absorption of nutrients. FIG. 4B depicts an example of a cross sectional view of the esophagus where it joins the stomach, and further depicts one variation of a tissue acquisition device of the present invention 105, actively engaging the tissue to be fastened in a circumferential fashion.

Method of Hollow Organ Volume Reduction

A clinical work-up, including a physical and mental assessment of the patient may be performed to determine whether a transoral stomach reduction clinically indicated. This assessment may include inspecting the esophagus and stomach of the patient to determine whether any contraindications exist for undertaking the procedure such as ulcerations, obstructions, or other conditions that may preclude treatment. Once the assessment has been completed, either in an operating room with the patient under general anesthesia, or in an endoscopy suite with the patient under sedation, the operator can introduce a tissue acquisition and fixation device, as shown in FIGS. 5A-5D, down the patient's esophagus and into the stomach to a location just beyond the GE Junction (GEJ). Once in place, an optional calibration device (not shown) such as a balloon or boogie can be inflated or deployed proximally or adjacently to the GE Junction (GEJ) to assist in correctly sizing the pouch to be created. Alternatively, the physician may opt to use direct vision and place an endoscope through the main lumen of the tissue acquisition device to view the site of entry and resultant treatment zone.

Figure 5A:
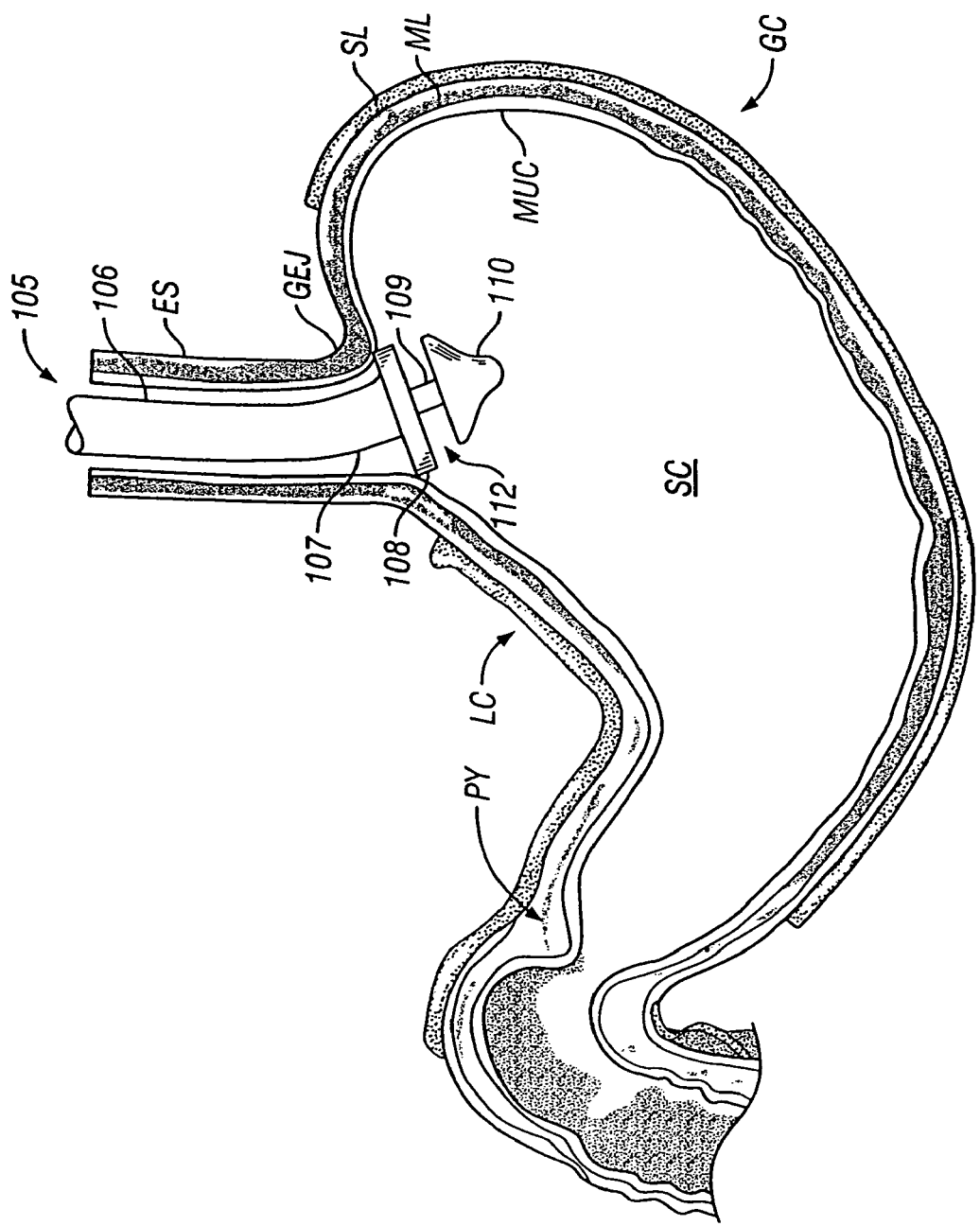
FIGS. 5A-5D depict one variation of procedural steps of performing the methods of the present invention, by showing a cross section of an organ (stomach) and the placement of the device to create a narrowing or "pouch" within the organ.

FIGS. 5A through 5D depict cross sectional schematic views of the procedure of the present invention showing tissue being manipulated within a hollow organ, the stomach. FIG. 5A depicts the esophagus (ES) the stomach cavity (SC), including the landmarks of the lesser curve of the stomach (LC), the gastroesophageal junction (GEJ), and the pylorus (PY). Tissue layers represented are the serosal layer (SL), the muscularis or fibrous muscular layer (ML), and the mucosal layer (MUC). Further, FIG. 5A shows the tissue acquisition device 105 positioned within the esophagus at a location within the stomach cavity (SC) between the lesser curve (LC) of the stomach and the GEJ.

The device 105, includes a main body 106 having at least one lumen therethrough (not shown), an outer portion 107, having a distal end 108 containing a fixation mechanism and a proximal end (not shown). The device 105 further comprises an inner portion 109, which has a distal portion 110 containing a fixation mechanism and a proximal portion (not shown) received therein. Once device 105 is positioned in the preferred anatomical location, outer portion distal end 108 and inner portion distal end 110 are separated by relative movement of inner portion 109 within outer portion 107, to expose opening 112. As described in further detail later below, opening 112 is operatively connected to at least one lumen within the main body 106 and provides a force, e.g., a vacuum force, to facilitate tissue acquisition. Such a force may be provided by a vacuum or by a mechanical element.

Figure 5B:
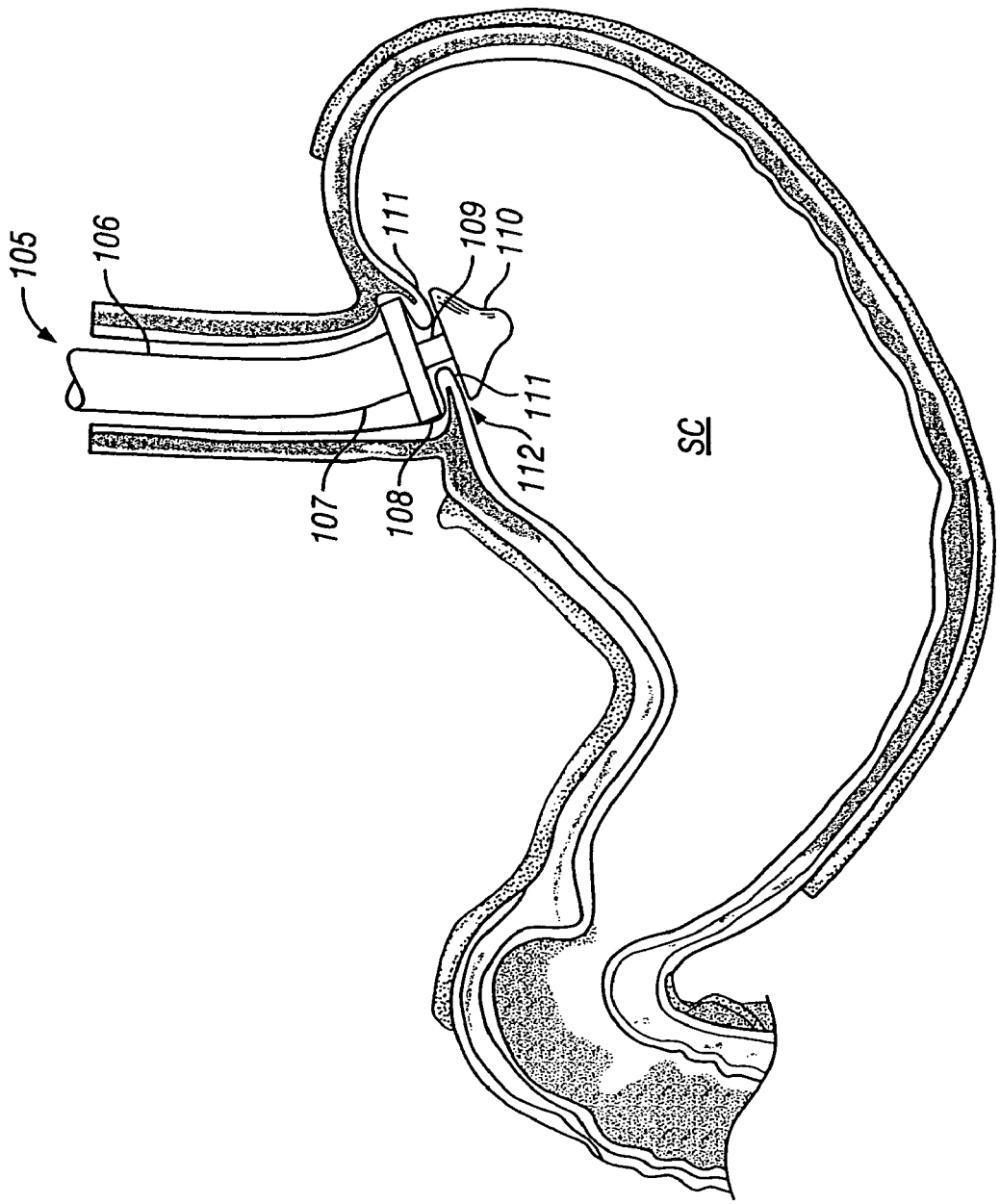

As shown in FIG. 5B, in the case of vacuum, once the opening 112 is exposed to the surrounding tissue within the stomach cavity (SC), the vacuum may be activated and tissue 111 may be drawn into the opening 112 in an entirely circumferential manner or a substantially circumferential manner, i.e., at least partially about the circumference of the device at some point less than 360 degrees (possibly in a 180 degree formation) relative to a longitudinal axis of the device. The amount of tissue 111 acquired can vary, but the amount drawn is preferably sufficient enough to result in healing of the fastened sections, thereby creating a tissue ring (TR) around the circumference of the fastened tissue. Said tissue ring may be formed of various layers of the stomach and may include scar tissue and other elements of effective wound healing.

Figure 5C:
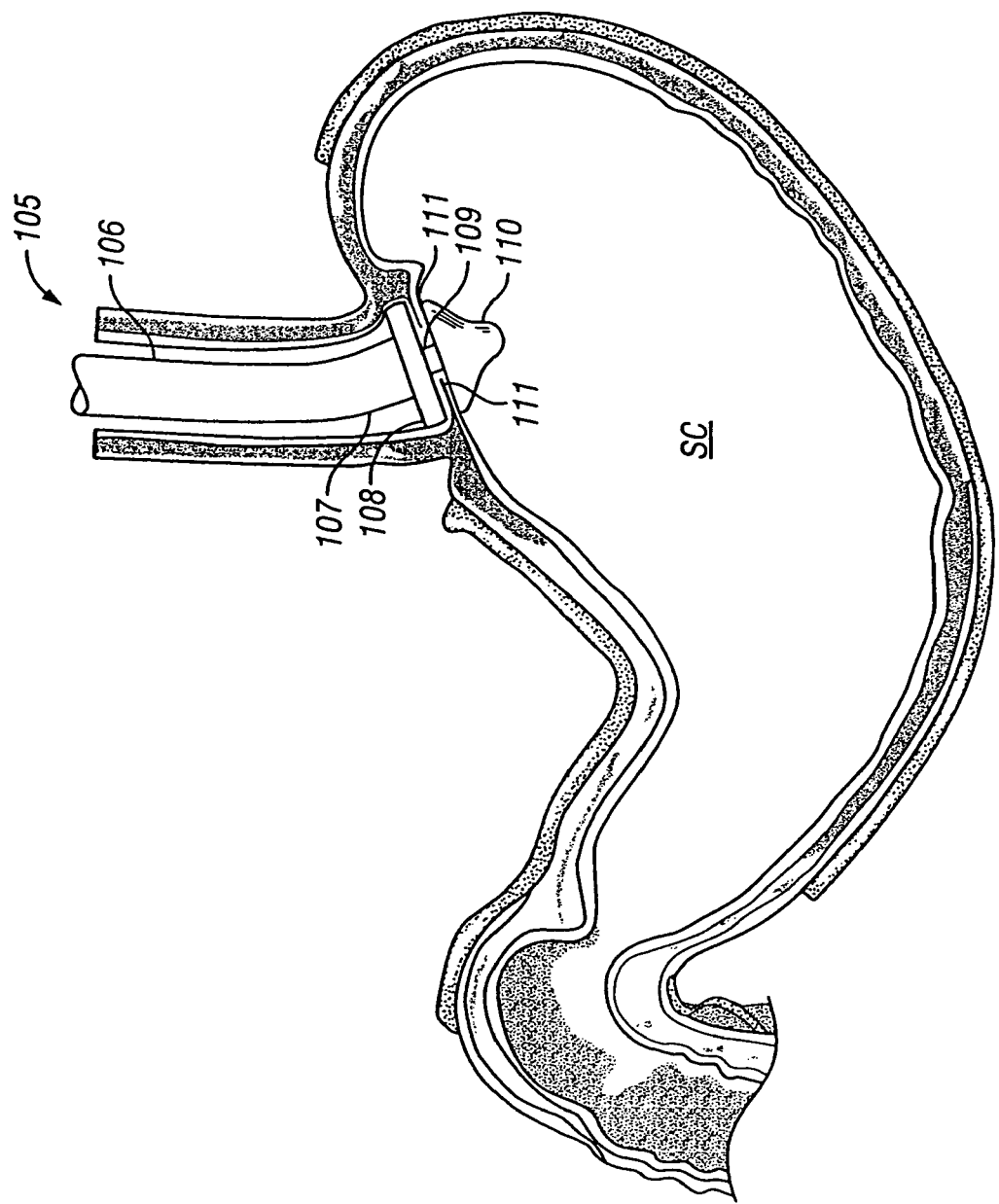
Figure 5D:
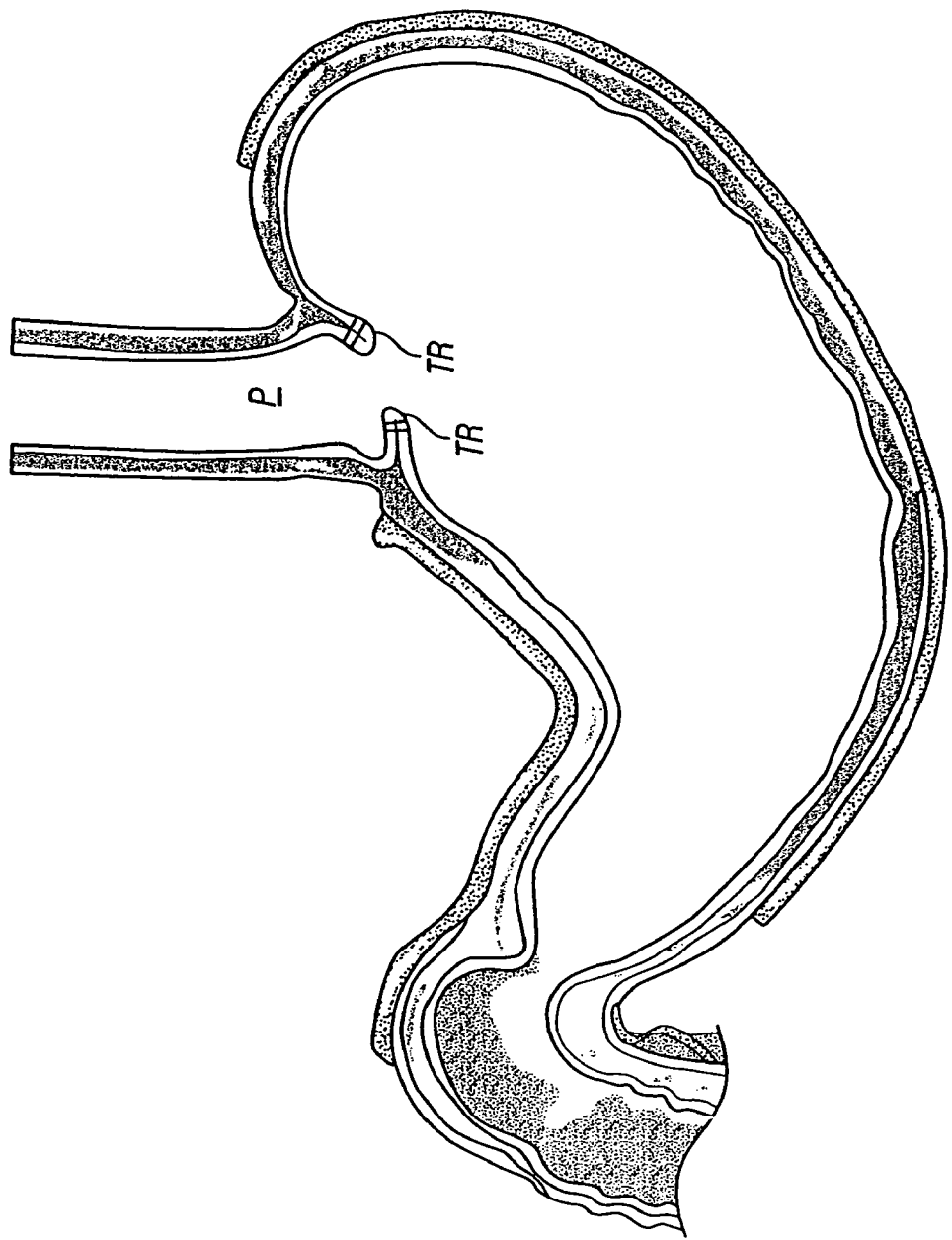

FIG. 5C further depicts the device 105 after the desired amount of tissue 111 has been acquired, outer portion distal end 108 and inner portion distal end 110 may be moved towards one another such that the acquired tissue 111 is clamped therebetween. Device 105 is then actuated to engage at least one fastening element (not shown) through the acquired tissue 111 thereby fastening it in place in a circumferential fashion. This fastening step may also include a cutting step to score or otherwise abrade the acquired tissue 111 after it is fastened to enhance the healing response of the tissue 111 to increase the durability of the tissue ring. In addition, bulking agents, such as collagen, may be injected at the time the stoma is formed, or thereafter, to aid in healing and durability of the tissue. Once the tissue 111 has been fastened or fixed, the tissue acquisition device 105 is then removed. In doing so, the inner portion distal end 110 of the device may be carefully pulled through the newly-created tissue ring or stoma created by the procedure so as to minimize stretching of the ring or stoma. Finally, FIG. 5D depicts the stomach showing the final result and placement of a circumferential tissue ring (TR) or stoma (ST).

Figure 5E:
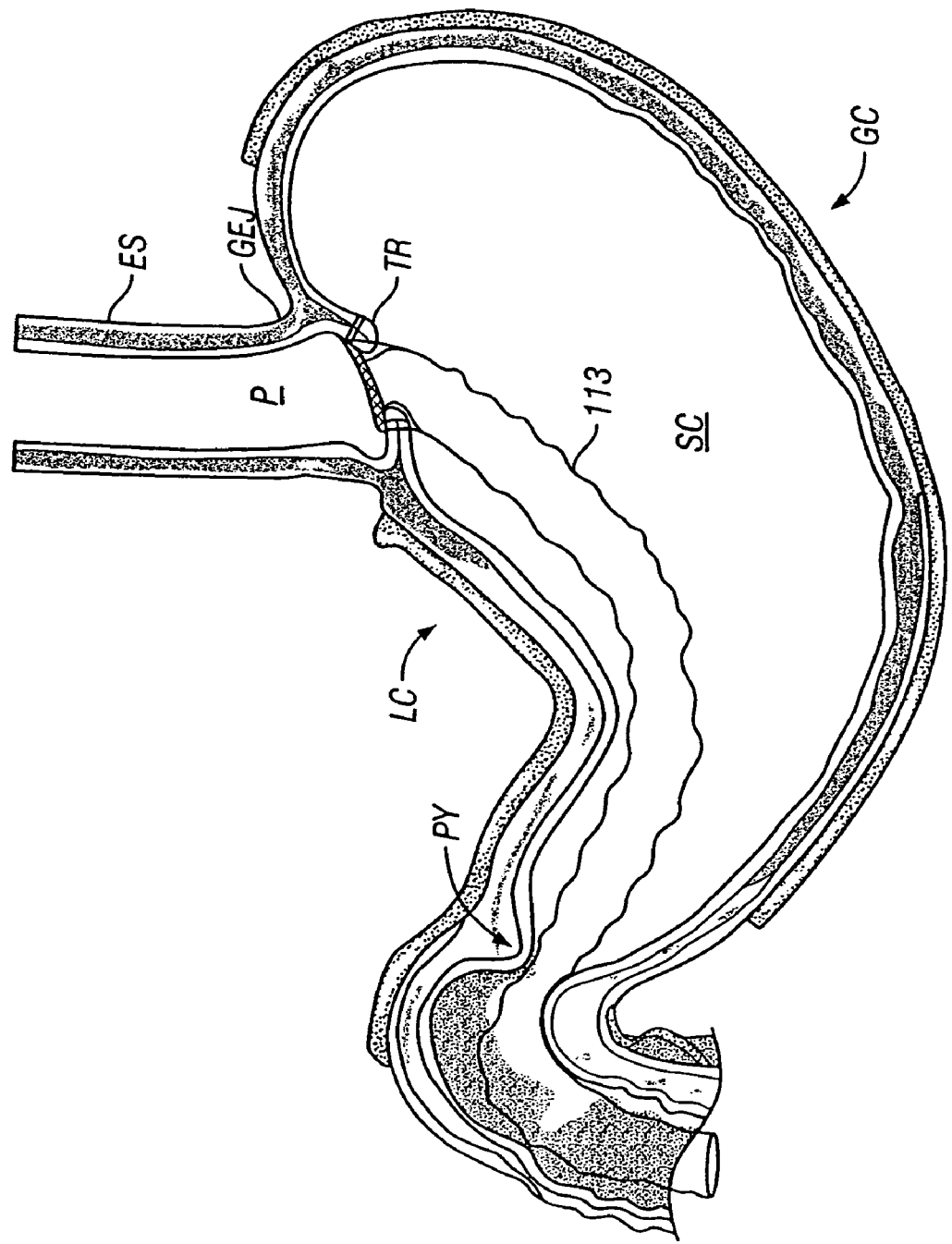
FIG. 5E depicts one variation of a result of the present invention, including a bypassing sleeve installed to bridge from the point of the stoma at the GEJ, to the pylorus, or further into the intestine.

As depicted in FIG. 5E, it is also contemplated that the procedural steps described above may be followed by the placement of an optional bypass conduit 113 to create a bypass from the newly created pouch (P) directly to the pylorus (PY) or beyond into the small intestine. Such a bypass would channel food directly from the pouch (P) into the small intestines to achieve a malabsorptive effect in cases where such an effect may enhance weight loss. Such a bypass conduit 113 may be formed of any suitable biocompatible graft material such as polyester or PTFE, and may be secured to the newly created tissue ring (TR) or stoma (ST) endoscopically using a clip or stent like structure at the anchored end to produce an interference fit within the stoma. Alternatively, the bypass conduit could be placed over the acquisition device of the present invention, and secured by the same fastening elements, and at the same time as the formation of the stoma. In doing so, the end of the bypass graft to be anchored may be placed over the tissue acquisition device such that the end of the graft coincided with the tissue acquisition device opening 112, allowing it to be acquired into the device and fastened along with the surrounding tissue. Similarly, the bypass conduit may be anchored in the pylorus (PY) or intestine by similar methods, or may just be left unanchored in the intestine to allow for movement due to peristalsis of the intestinal wall.

FIGS. 6A-6D depict variations of the tissue rings and pouches created using the method, and variations thereof, described herein. FIGS. 6A and 6B depict the results of utilizing the procedure described above, showing a complete circumferential ring, in this variation, created just distal from the where the esophagus (ES) and the stomach join each other. FIG. 6B shows a cross section of the stomach and tissue ring (TR) and further depicts the resulting tissue folds 114 acquired by the device 105 and the fixation elements 115 deployed to fix the acquired tissue. This cross section further depicts a cut zone or abraded zone 116 as described above. FIGS. 6C and 6D depict another variation in which fixation of the acquired tissue in a position centered between the lesser curve of the stomach (LC) and the greater curve (GC) in such a manner that multiple lumens 117, 118 result as shown in FIG. 6D. Although only two additional lumens 117, 118 are shown in this variation, a number of lumens may be created in other variations depending upon the number of times and positions the tissue is affixed.

One method of the present invention is to use the device 105, or a variation thereof, to modify or otherwise assist in other procedures that utilize stomach or organ plication such as those described in co-pending U.S. patent application Ser. No. 10/188,547 earlier incorporated herein by reference, which describes, in part, in further detail methods and devices for stapling regions of the stomach in a linear fashion. In cases where a zone of the stomach is linearly stapled, the device 105 may be employed to create circular stomas at either end of the linear staple line so as to enhance the efficacy of a volume reduction procedure or to enhance durability of the staple line. It may also be advantageous to place semi-circular or partially circumferential fixation zones at various locations within the target hollow organ. The devices and methods described herein are particularly well-suited for this because of their ability to "gather" the tissue and create a circumferential restriction that acts to limit the flow of matter, such as food, through the organ.

Devices

Figure 7A:
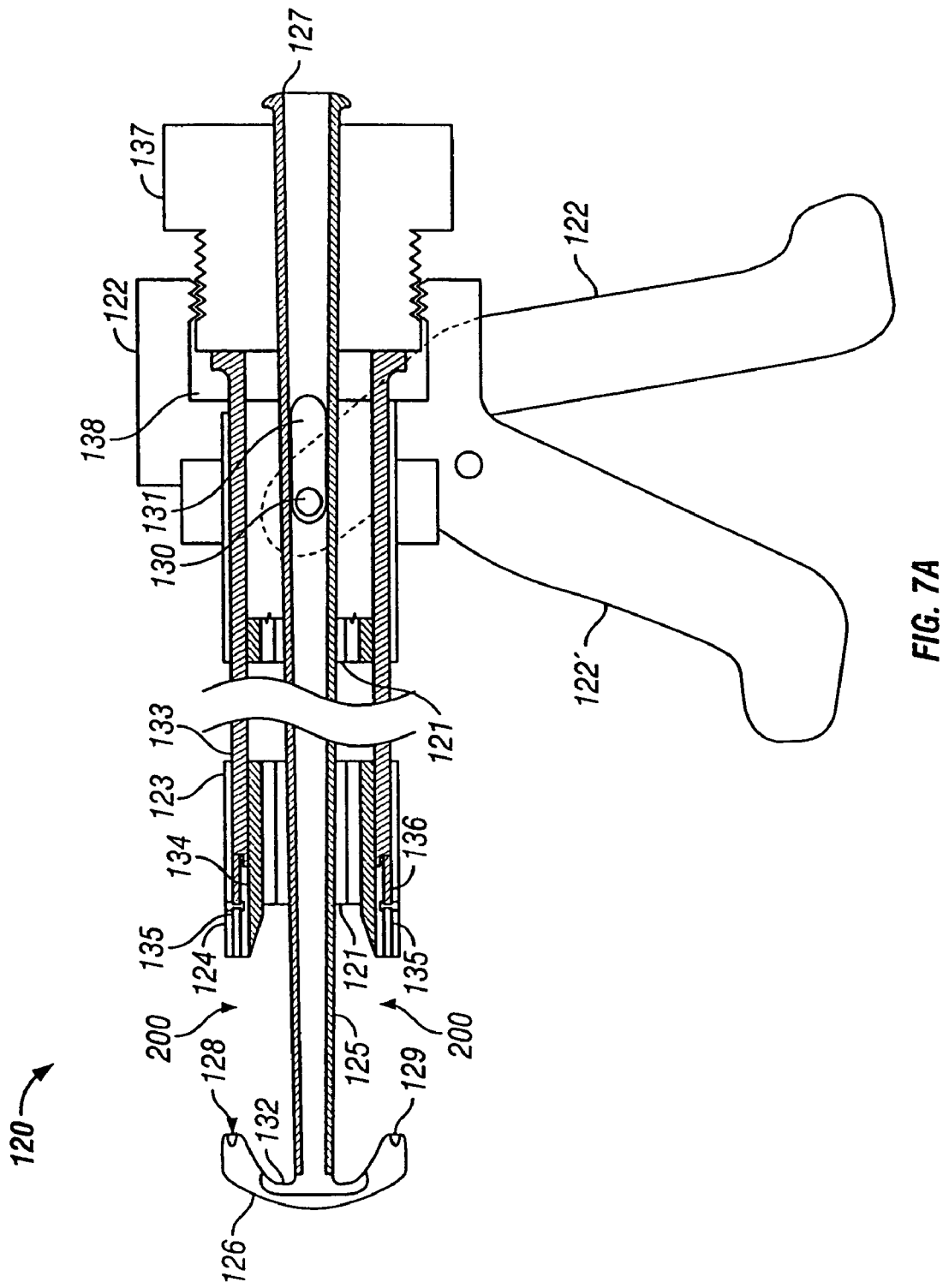

FIG. 7 depicts a cross-sectioned view of one variation of tissue acquisition device 120. As shown, device 120 has a main body portion 123 which has a proximal end, a distal end, and a main lumen 121 defined therethrough. Device 120 also has a grip portion 122' and an opposing handle portion 122 which may be pivotally attached to main body portion 123 such that handle portion 122 is angularly positionable relative to grip portion 122'. Main body portion 123 may further define one or more circumferentially defined lumens along its length such that these lumens terminate at the distal end of body portion 123 at outer distal portion 124. Main body portion 123 further houses main body inner portion 125, which may be an elongate tubular member configured to be slidably positioned within main body lumen 121 defined through the length of main body portion 123. At the distal end of inner portion 125, an inner body distal portion 126 may be attached thereto. This distal portion 126 may be integrally formed onto inner portion 125 or attached separately and may be used as a clamping member to facilitate the mechanical retention of tissue invaginated into the device 120. Distal portion 126 may also function as an anvil for reconfiguring fastening members inserted into the tissue, as further described below. The proximal end of inner portion 125 may terminate proximally of main body portion 123 in a fluid port 127, which may be utilized for fluid connection to, e.g., a vacuum pump (not shown). Alternatively, distal portion 126 may function as the staple housing and outer distal portion 124 may function as the opposing anvil. In this variation, the fasteners, as positioned within distal portion 126, may be deployed through inner face 128 into the tissue using an actuation device, as known in the art.

Figures 7B, 7C:
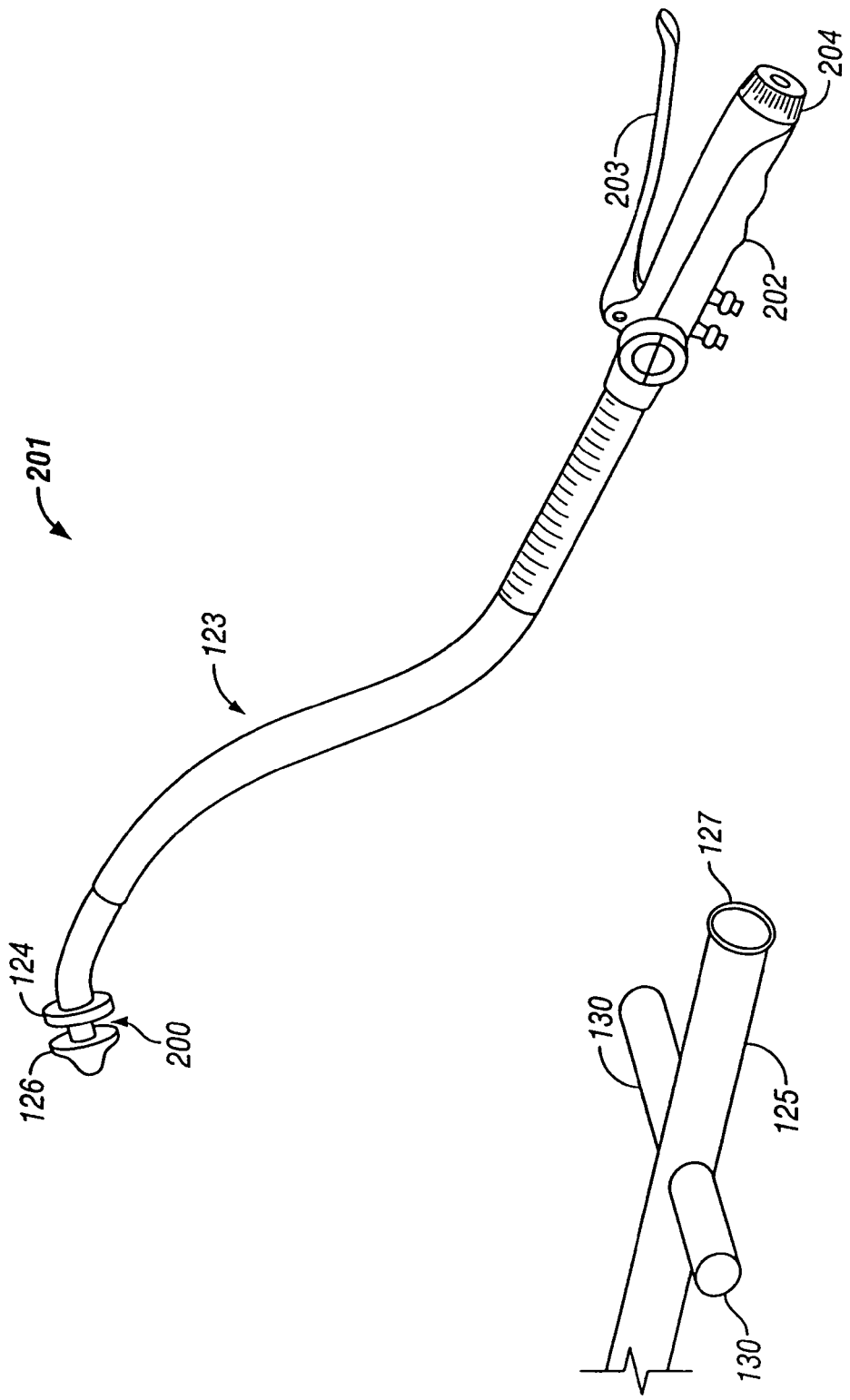

Inner body distal portion 126 may further comprises an inner face 128 which may define an anvil or fastener element detent 129. Where inner portion 125 joins with distal portion 126, one or more distal ports 132 may be defined which are in fluid communication through inner portion 125 with fluid port 127. To actuate device 120, handle portion 122 may be urged to pivot relative to grip portion 122'. Slider pins 130 may be fixedly attached to main body inner portion 125 and configured to extend perpendicularly relative to inner portion 125, as shown in FIG. 7B. Pins 130 may be operatively connected with handle 122 such that rotation or movement of handle 122 is translated into the linear motion of inner portion 125. Pins 130 may be positioned within slot 131 which are defined longitudinally within main body portion 123. Slots 131 may be configured to allow limited translational movement of pins 130 thereby limiting the overall translational distance traveled by inner portion 125.

Actuation of handle 122 in a first direction may urge pins 130 to slide within slots 131 a first direction, e.g., distally, thereby moving inner portion 125 distally, and actuation of handle 122 in a second direction may urge pins 130 to slide in a second direction, e.g., proximally, thereby moving inner portion 125 proximally. Main body inner portion 125 may be actuated to linearly move inner body distal portion 126 relative to outer distal portion 124 to a desired distance between the two. When the two portions 124, 126 are moved into apposition to one another, a circumferential tissue acquisition chamber or space 200 may be created about or defined between the outer surface of inner portion 125, inner distal portion 126, and outer distal portion 124. Space 200 may be in fluid communication with distal port 132 and/or optionally through main body lumen 121. In operation, a vacuum force may be applied through distal port 132 and/or main body lumen 121 to invaginate or draw tissue into space 200 such that the tissue is held or configured to then receive at least one fastening element to affix the tissue configuration.

Main body portion 123 may further house driver element 133 within circumferentially-shaped fastener lumen 134. Driver element 133 may be a tubularly shaped member which is configured to traverse longitudinally within fastener lumen 134. Disposed distally of driver element 133 within fastener lumen 134 are fasteners 135 and fastener pusher mechanism 136. Fasteners 135 may comprise any variety of staples or mechanical fasteners which are made from a biocompatible material, e.g., stainless steel, platinum, titanium, etc., and fastener retention mechanism 136 may also comprise any variety of staple retainer which is configured to hold fasteners 135 within fastener lumen 134 until fasteners 135 have been pushed or urged out of the lumen 134 and into the tissue. The proximal end of driver element 133 abuts driver actuator 137 in handle portion 122. Handle portion 122 may define a threaded cavity 138 at its proximal end which is configured to correspondingly receive and is in operative communication with driver actuator 137, which may also define a threaded insertion surface for mating with threaded cavity 138. In operation, upon tissue acquisition within circumferential space 200 and approximation of main body inner distal portion 126 and main body outer distal portion 124, driver actuator 137 may be rotated in a first direction so as to matingly engage the threads of handle portion threaded cavity 138 and thereby engage the proximal end of driver element 133 to cause driver element 133 to move distally. As driver element 133 is advanced longitudinally in a corresponding manner as driver actuator 137 is rotated, the distal end of driver element 133 may contact fastener pusher mechanism 136 and actuating fastener 135 to distally advance and deploy fastener 135 into any acquired tissue.

Main body portion 123 may be bendable as depicted in FIG. 7C. As shown, the device 201 may be seen in one configuration in which main body portion 123 may be configured in an infinite number of different configurations for negotiating pathways within a body. This particular variation 201 shows handle grip 202 having an opposing actuation handle 203 for actuating movement of inner body distal portion 126. Also shown is an optional scope lumen 204 in the handle 202 which may be used for visualizing the tissue region being treated during deployment or actual treatment. The flexibility of the main body portion 123 may be imparted, in part, by the use of, e.g., linking multiple rings 211, as shown in the isometric view in FIG. 7D. A portion 210 of the main body 123 is shown with the covering, control mechanisms, etc., omitted for clarity. Although this variation shows the use of stacked multiple rings, other variations may also be used as known in the art for flexible and/or articulatable elongate devices, e.g., endoscopes, etc. A plurality of individual rings 211 may be aligned with one another to create a length of the main body portion 123. Any number of rings 211 may be used depending upon the overall desired length of the device or the desired length of a flexible portion of the device. Each of the rings 211 may have at least one main channel or lumen 212, which when individual rings 211 are aligned as a whole, create a main channel throughout the length of the device. Each of the rings 213 may also have a number of spacers or protrusions 213 defined on or around the circumference of the device for creating pivotable sections for facilitating relative motion between adjacent rings 211, as known in the art. Although the rings 211 are shown with two oppositely positioned protrusions 213, any number of protrusions 213 may be used as practicable depending upon the degree of relative motion desired between adjacent rings 211. Alternatively, device main body 123 may be constructed in part of, e.g., a coil spring, to achieve a similar functional result. Coil springs may be made of superelastic materials, e.g., nitinol, or spring steels made, e.g., from stainless steels. The main body 123 or main body segments may be constructed of various biocompatible materials, such as stainless steel, Delrin or other engineering thermoplastics, etc.

FIG. 7E depicts a single ring 211 having the main lumen 212 defined therethrough. Main lumen 212 may be modified and enlarged to provide a channel having a large enough diameter to receive a conventional endoscope for possible use with the present device. One example of such a device may have a lumen diameter of, e.g., 10 mm, with an outer diameter of, e.g., 18 mm. One or more of such lumens may be created within the annular section 211 to enable linkage of each section 211 to one another by one or several cables or flexible wires (not shown) adapted to be positioned through the lumens. These wires or cables may be routed through the length of the device and fixed at the proximal end of the main body portion 123.

Figure 7F:
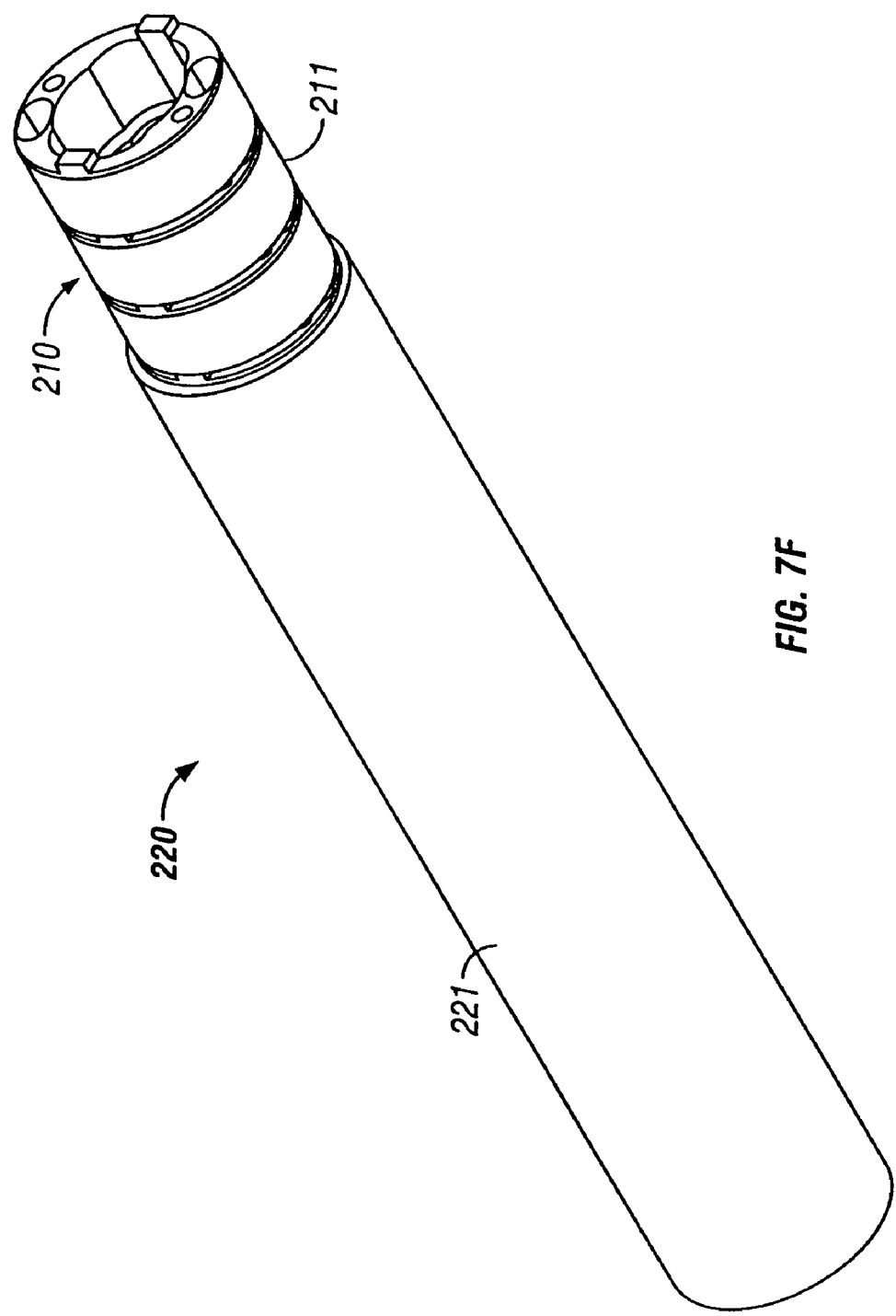

As shown in FIG. 7F, an optional sheath or thin film 221 may be placed over the device or at least along a portion 210 of the device to encapsulate the linkages and create a smooth shaft surface, while still maintaining its flexibility. The sheath or thin film 221 may be made of a variety of biocompatible materials, e.g., heatshrink polymers, plastics, etc.

Figure 8:
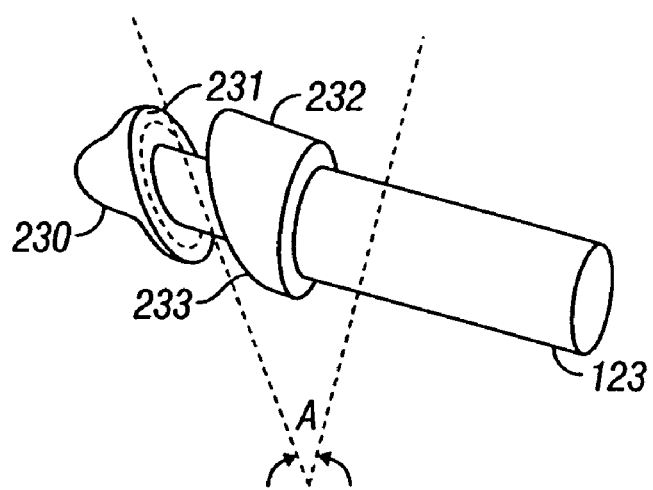
FIG. 8 depicts details of one variation on the distal portion of the circular tissue acquisition and fixation device of the present invention showing an angled annular acquisition space.
Figure 9:
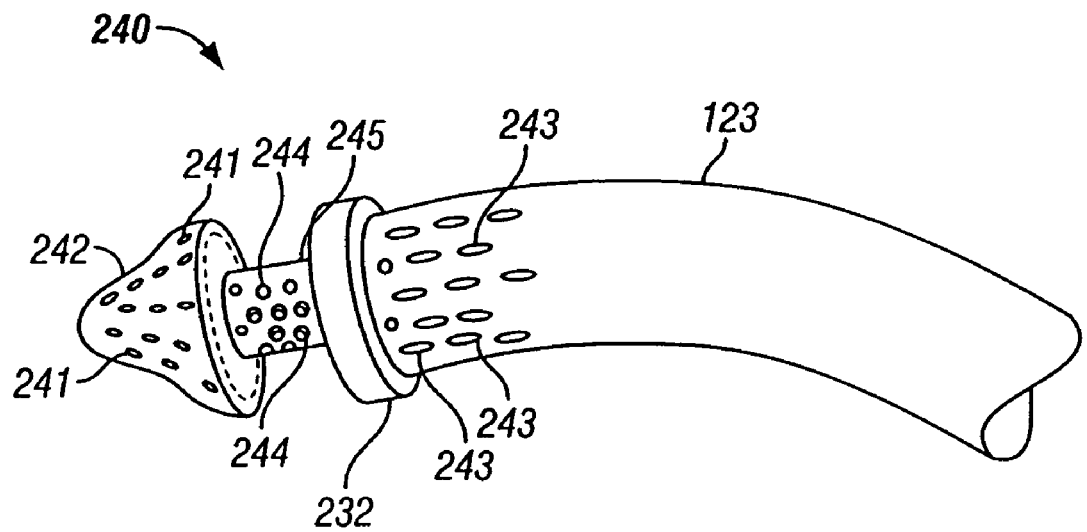
FIG. 9 depicts another variation of the tissue acquisition mechanism of the circular tissue acquisition and fixation device of the present invention.

FIG. 8 depicts another variation on the distal end of a tissue acquisition device. The inner distal portion 230 is shown defining an inner face 231 and device outer distal portion 232 having an inner face 233. The inner distal portion inner face 231 and the outer distal portion inner face 233 may be formed to face one another in apposition and both faces 231, 233 may each be formed at an angle (A) relative to a longitudinal axis of the device main body 123. The angle (A) may range anywhere from 0-90 degrees, but is preferably in the range of 15-45 degrees, depending on the desired angle of the resulting tissue fixation zone. This variation may be used to allow the operator to position the tissue acquisition device perpendicularly to a surface of the organ to be treated (for ease of use) while acquiring and fixing the tissue at an angle relative to the tissue surface. In doing so, the operator may fashion the resulting fixation zone to more closely approximate a curvature of the organ, such as the curvature between the GEJ and the LC of the stomach. FIG. 9 depicts a further variation 240 of the tissue acquisition device in which fenestrations or ports 241 may be defined over the surface of the device inner distal portion 242. Additional fenestrations or ports 243 may be defined over a portion of the device outer distal portion 232, and additional fenestrations or ports 244 may also be defined over a surface of body inner portion 245. These additional ports may allow this variation 240 to acquire tissue along a length of the distal end of the tissue acquisition device 240 at multiple locations therealong. In practice, this method of tissue acquisition may allow the operator some freedom to manipulate the acquired tissue by the relative movement of device inner distal portion 242 and the device outer distal portion 232. This technique can also assist in positioning the tissue to be fixed, and/or assuring that the required amount of tissue (e.g. some muscular layers of the organ wall), have been uniformly acquired prior to fixation.

Figure 10A:
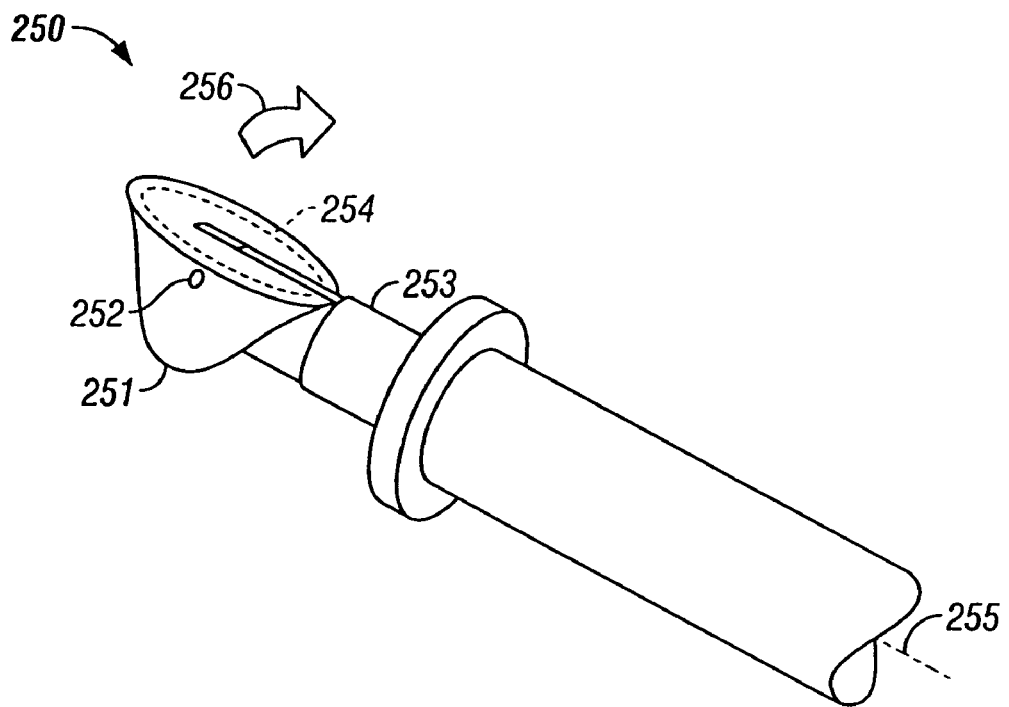
FIGS. 10A-10B depict variations of the distal working end of the distal tip of the circular tissue acquisition and fixation device of the present invention, detailing an anvil designed to be intraprocedurally manipulated to assist in removal of the circular tissue acquisition and fixation device of the present invention once the desired tissue has been acquired and fixed according to the present invention.
Figure 10B:
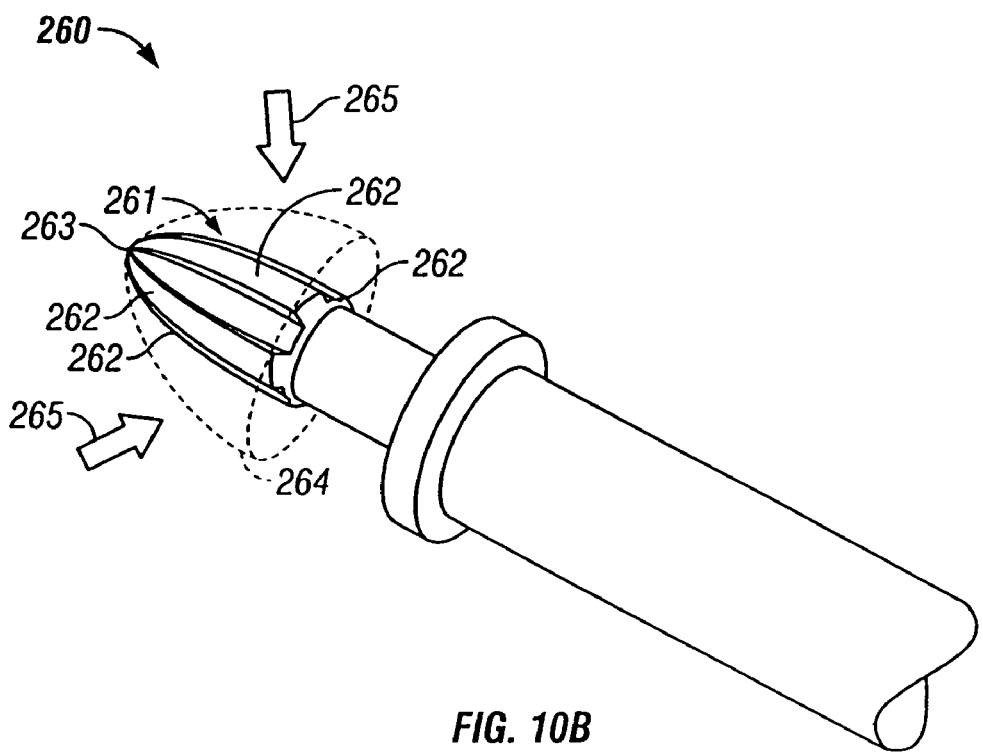

Following fixation, the tissue acquisition device of the present invention is withdrawn from the organ. In doing so, care should be used not to over-dilate or stretch the newly created tissue ring or stoma. To mitigate any dilation or stretching, the inner distal portion may also be modified. FIGS. 10A and 10B depict variations 250, 260 of the tissue acquisition inner distal portion that are adaptable to effectively reduce in cross sectional area to allow for easier removal of the tissue acquisition device from the organ once the circumferential fixation zone has been created. FIG. 10A depicts tissue acquisition device inner distal end 251 which is pivotally mounted on main body inner portion 253 about pin 252. Activation of the pivoting action may be controlled by release of an interface between pin 252 and a stay (not shown) housed within main body inner portion to activate rotation of inner distal end 251, e.g., in a direction 256. The inner distal end 251 may be rotated by any angle such the inner face 254 is angled or parallel relative to the longitudinal axis 255 of the device.

FIG. 10B depicts another variation 260 on tissue acquisition inner portion distal end which may have a segmented configuration. In this variation 260, the inner portion distal end may be made of a plurality of individual segments 262 which when collapsed, reduces the diameter of inner portion distal end to facilitate removal. Thus, during tissue acquisition and/or fixation, the expanded inner distal portion 264 may be utilized and after the procedure, it may then be compressed radially 265 about a pivot 263 to reduce the cross-sectional profile for removal from the area.

Additional Bypass Conduit Devices

Figure 11A:
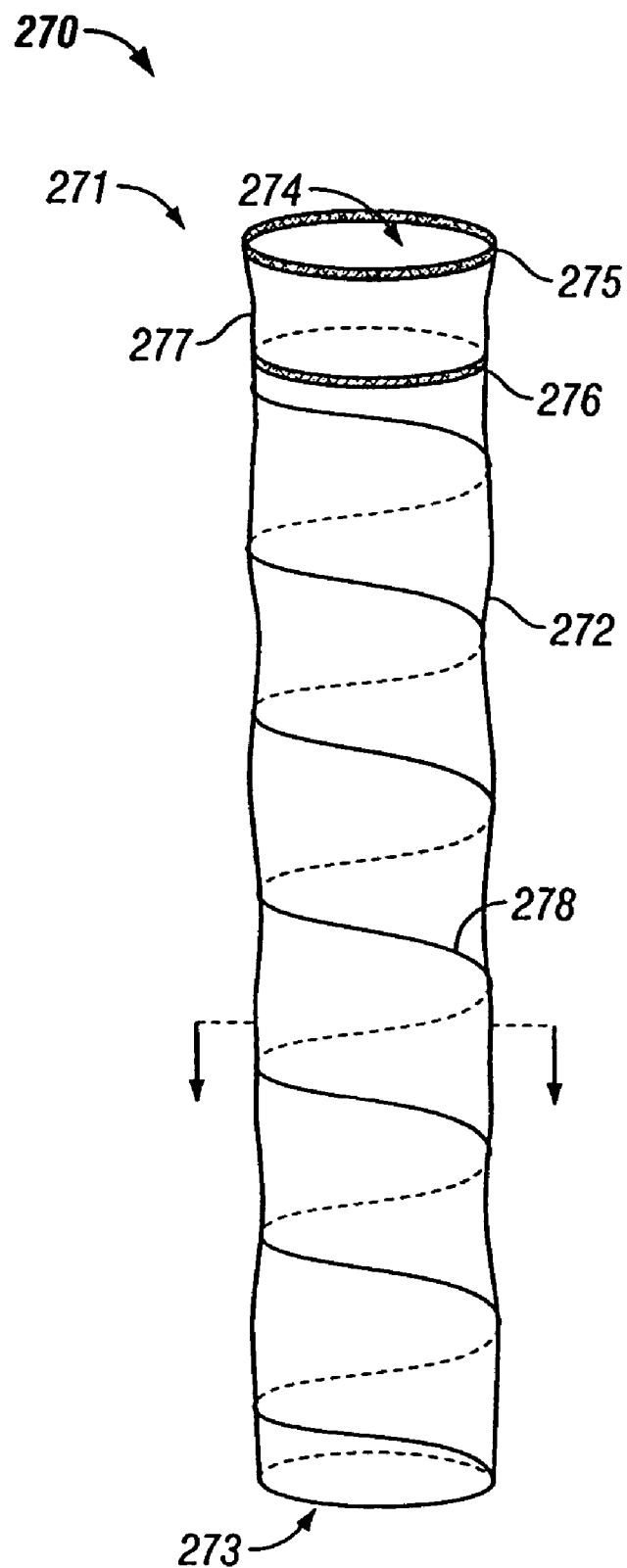
FIG. 11A depicts a variation of a bypass conduit assembly.

As mentioned above for FIG. 5E, an optional bypass conduit 113 may be placed within the stomach cavity (SC) at the site of the narrowing or stoma (ST). Such a conduit may be placed not only in conjunction with the intragastric staple line described herein, but with various other conventional procedures to create a bypass from the pouch (P) directly to the pylorus (PY), or beyond into the small intestines to effect the rate at which food is metabolized. It may also further enhance the efficacy of a bariatric procedure by facilitating "dumping syndrome". One variation on the bypass conduit is seen in FIG. 11A in bypass conduit assembly 270. In this variation, assembly 270 comprises a conduit wall 272, which may be tubular in shape. Bypass lumen 274 may be defined throughout the length of conduit wall 272. The conduit wall 272 may extend between a proximal end 271 and to a distal end 273 and may be made from a variety of biocompatible materials. For instance, conduit wall 272 may be made from a rubber material or from a polymeric material which may be configured to be lubricious, e.g., Teflon, Nylon, Dacron, PTFE, polyethylene, polystyrene, polyurethane, polyethylene terephthalate, etc.

To further increase the structural resiliency of the conduit wall 272, an optional reinforcing member 278 may be utilized within the structure. Reinforcing member 278 may include any number of structural enhancements such as a coil member as shown in the FIG. 11A. The coil member may be wound in a helical manner along the body of conduit wall 272 either along the entire length or a portion of the length of conduit wall 272. Another variation may have wires positioned longitudinally along conduit wall 272 rather than a coiled member. Alternatively, a wire-framed structure may be utilized along the conduit wall 272.

In any of these structural enhancements, the reinforcing member 278 may be disposed in a laminate structure between layers of conduit wall 272 material. Alternatively, the reinforcing member 278 may be formed integrally into the conduit wall 272 by forming the conduit material about the member 278. Another variation may have reinforcing member 278 adhered onto the outer and/or inner surface of the conduit wall 272 through the use of adhesives, sutures, clamps, or any other number of conventional attachment methods. Moreover, these optional structural enhancements may be utilized not only in the variation shown in FIG. 11A, but in any of the other variations described herein depending upon the desired structural characteristics.

The proximal end 271 may be affixed or secured to the stomach tissue within stomach cavity (SC), to the tissue adjacent to pouch (P), or to other tissue, as further described below. In the present variation, conduit assembly 270 may have a first gasket 275 and a second gasket 276 positioned distal of the first gasket 275 along wall 272. Gaskets 275, 276 may be made of a rubberized material or a polymeric material configured to be flexible during the deployment of assembly 270. Such a gasketed assembly 270 may be used in conjunction with the tissue ring (TR) or stoma (ST), as described in detail above. Upon deployment and positioning of assembly 270 within the stomach cavity (SC), these gaskets 275, 276 may be allowed to expand such that first gasket 275 is located proximally of the stoma (ST) and second gasket 276 is located distally of the stoma (ST). A portion of the conduit wall 277 located inbetween the gaskets 275, 276 may be in contact with the stoma (ST) and may be sufficiently flexible to form around the stoma (ST).

When the bypass conduit is properly positioned to extend from the narrowing, e.g., the stoma, to within the intestinal tract, e.g., to the jejunum or farther, the distal end of the liner may be positioned to extend distally of the duodenal ampulla 323. As explained in further detail below, the duodenal ampulla is a duct which connects the common bile duct and the pancreatic duct to the duodenum for discharging digestive fluids into the duodenum. These fluids (alimentary flow) normally intermix with partially digested food from the stomach cavity (SC). To facilitate such fluid exchange and to prevent the duct from being blocked by the liner, the liner may include communications to the inside of the liner, such as fenestrations, or channels alongside the liner wherein the cross section of the liner may be varied to allow such an exchange.

Figure 11B:
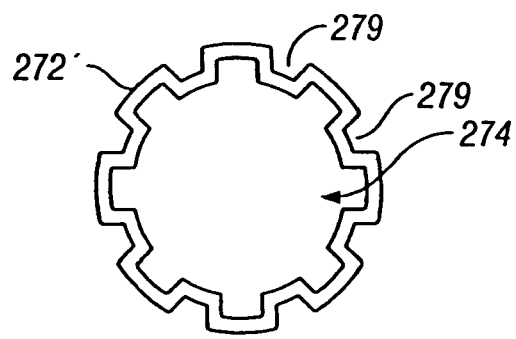
FIGS. 11B-11E depict variations on possible cross sections of the bypass conduit assembly.
Figure 11C:
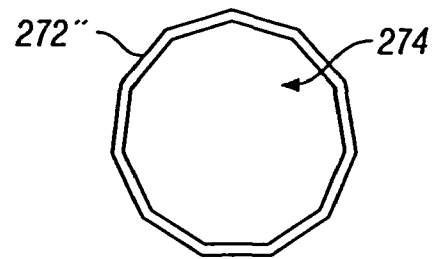
Figure 11D:
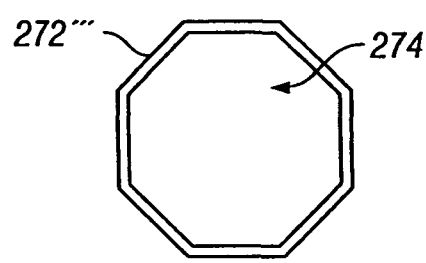
Figure 11E:
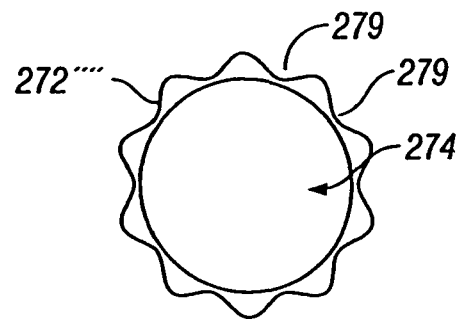

FIGS. 11B-11E show variations of cross sections of the bypass conduit from FIG. 11A which may allow for fluid exchange to occur along the outer surface of the liner. FIG. 11B shows one variation in which the conduit wall 272' defines one or more longitudinal channels 279 along the outer surface of the wall 272'. FIGS. 11C and 11D show variations in which the conduit walls 272", 272''', respectively, are angled such that the contact between the outer surface and the tissue is non-continuous, thereby allowing fluids to seep within or along these spaces or channels created between the angled outer surface and the tissue. FIG. 11E shows yet another variation in which the conduit wall 272'''' defines an undulating outer surface forming at least one or more longitudinal channels 279. These examples of possible irregularly defined cross sections are merely illustrative and are not intended to be limited only to these examples. Other variations, as should known to those in the art, are intended to be included therewithin.

As shown in FIG. 11F, these irregular cross sectional areas may extend along the entire length of the conduit wall 272' or just partially along the conduit wall 272', as shown. The length of the irregular cross section may extend just from within the body organ to distal of the body organ, or along any desired length of the conduit wall 272', depending upon the desired results.

Another variation on the bypass conduit is shown in FIG. 12 in conduit assembly 280. This variation is similar to that shown in FIG. 11A but with the addition of a fluid bypass conduit 281 located adjacent to conduit wall 272. The fluid conduit 281 has a proximal end 282 for positioning within the stomach cavity (SC) and a distal end 283 for positioning within the intestines distal to the stomach cavity (SC), as described in further detail below. Fluid conduit 281 may be made in a variety of ways; for instance, conduit 281 may be manufactured separately from conduit wall 272 and attached to the outer surface of the conduit wall 272 using any variety of methods, e.g., adhesives, clamping, etc., in which case conduct 281 may be made from a similar or same material as conduit wall 272. For instance, fluid conduit 281 may be made of a braided material, as described above, to inhibit kinking of the conduit. Alternatively, conduit 281 may be formed integrally with the conduit wall 272 as a uniform assembly.

In either case, conduit 281 has a length which is typically coterminous with the length of the main conduit wall 272 but may be less than or greater than the length of the main conduit. The conduit 281 may also be configured such that the conduit 281 doesn't block the alimentary flow from the ducts. The distal end 283 of the conduit 281 may thus terminate proximally of the distal end 273 of the conduit wall 272, or it may optionally terminate at or distally of the distal end 273, depending upon the desired structure and use. Although a single fluid conduit 281 is shown in the figure, any number of additional fluid conduits may be incorporated into the assembly. These additional fluid conduits may be aligned in parallel with conduit 281 or positioned variously about the circumference of the conduit wall 272. Moreover, the additional conduits may be made of various lengths depending upon the desired results. Furthermore, although fluid conduit 281 is shown as being parallel with main conduit wall 272, fluid conduit 281 may be positioned about conduit wall 272 in a helical or spiral manner, or it may be positioned in a variety of ways, e.g., such as a bent or hooked proximal end, etc.

Yet another variation is shown in FIGS. 13A and 13B, which show conduit assembly variation 290. This variation incorporates a fluid bypass conduit 291 which is coaxially positioned about a portion of conduit wall 272. Fluid conduit 291 has a proximal end 292 for positioning within the stomach cavity (SC) and a distal end 294 for positioning distally of the stomach cavity (SC). To maintain the coaxially adjacent lumen 295, support struts 293 may be positioned between fluid conduit 291 and conduit wall 272, as seen in FIG. 13A and 13B, which is a cross-sectional view taken from FIG. 13A. Support struts 293 may be positioned circumferentially between fluid conduit 291 and conduit wall 272 in a variety of configurations so long as coaxial lumen 295 is substantially unobstructed. Support struts 293 may be fabricated separately or integrally with conduit wall 272 and/or fluid conduit 291. Alternatively, struts 293 may be extensions of a laminated wireframe making up the tubular structure for conduit wall 272 and/or fluid conduit 291.

Figure 14:
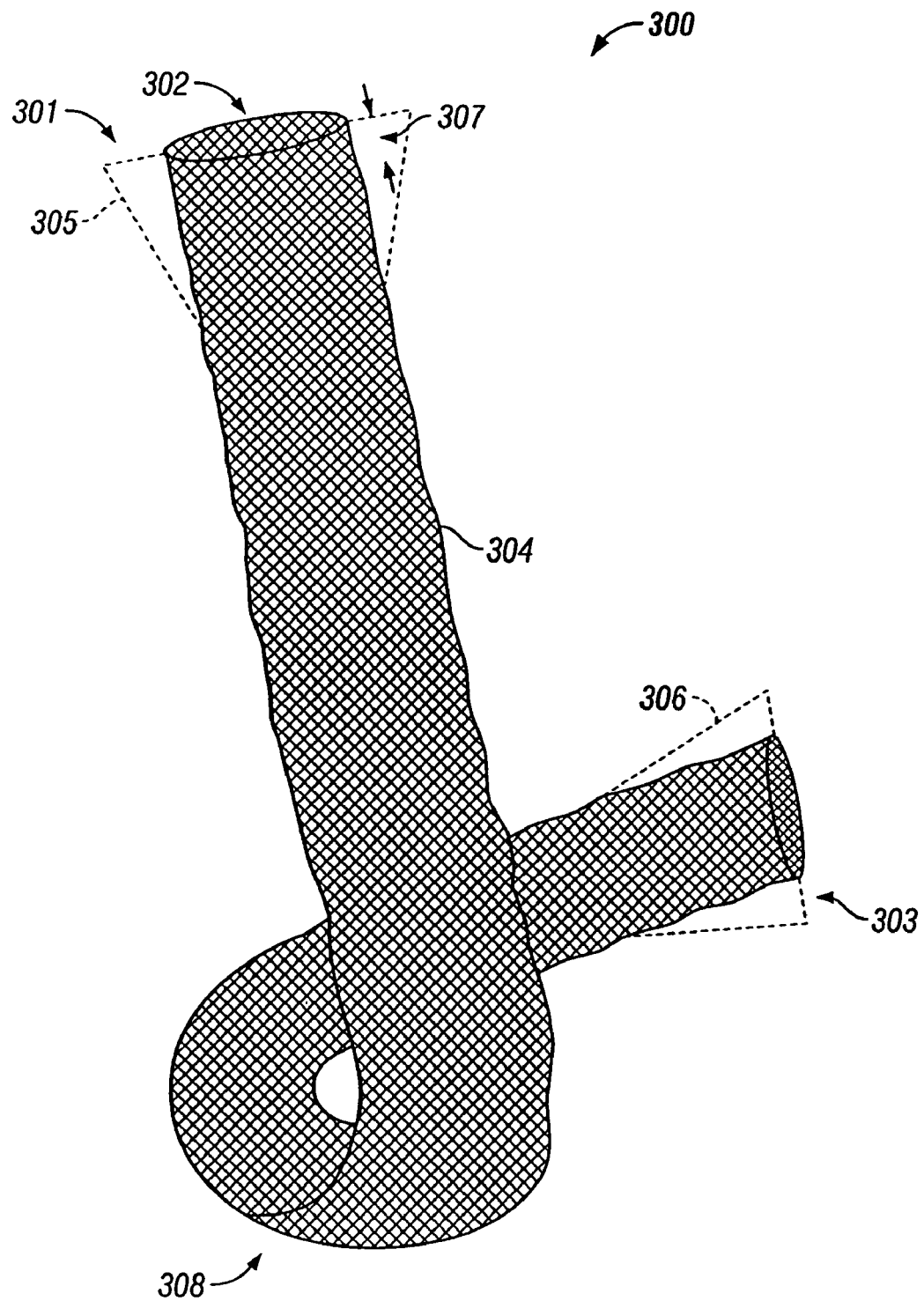
FIG. 14 depicts a perspective view of a braided tubular structure which may be utilized for the bypass conduit.

Conduit wall 272 and/or any of its auxiliary fluid conduits may be directly fabricated from various materials, as described above. Alternatively, they may be fabricated from an underlying braided tubular structure such as that shown in bypass conduit variation 300, as seen in FIG. 14. The walls of the conduit may be made of a braided material to form a braided tubular structure 304 defining a bypass lumen 302. The braided structure 304 may be made to make the assembly 300 more resistant to kinking, as is generally known in the art. The tubular structure 304 may be made, for instance, from superelastic materials like Nickel-Titanium alloys (nitinol) or from a metal such as stainless steel. Such construction may allow for the tubular structure 304 to be bent and twisted 308 in an infinite manner so as to allow the structure 304 to flex and move with the stomach without kinking or obstructing flow through the conduit. The braided structure 304 may be coated, covered, or laminated with a biocompatible material to aid in its lubricity; any variety of materials may be used, e.g., polymeric materials such Teflon, Nylon, Dacron, PTFE, polyethylene, polystyrene, polyurethane, polyethylene terephthalate, etc.

To aid in the secure placement of the bypass conduit proximal to or within the stomach cavity (SC), the proximal end 301 of the conduit 304 may optionally be radially flared 305 such that the flared portion 305 securely contacts the tissue. The flared portion 305 may optionally be reinforced, either by additional braiding or an additional structural ring or band, to create a reinforced region 307 for further ensuring adequate structural support. Moreover, the distal end 303 may also be optionally flared 306 to assist in anchoring the distal end of the bypass conduit within the intestinal tract or distal to the stomach cavity (SC).

Figure 15A:
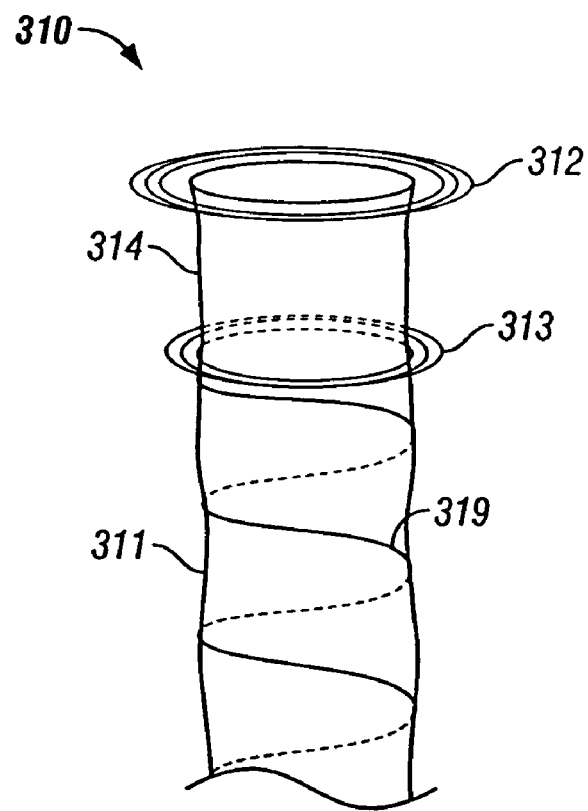
FIGS. 15A-15B depict variations on anchoring devices for the bypass conduit.

To further facilitate anchoring of a bypass conduit, a number of alternative anchors may be utilized aside from the gasketed configuration described above. Another variation is shown in FIG. 15A in conduit anchoring variation 310. As seen, conduit wall 311 may have a first gasket 312 and an optional second gasket 313 in which each gasket 312, 313 may comprise a coil which is biased to extend radially outward. As above, first and second gaskets 312, 313 may be separated by a conduit portion 314 and a partial length or the entire length of the conduit wall 311 may be reinforced with a reinforcing member 319, as described above.

Figure 15B:
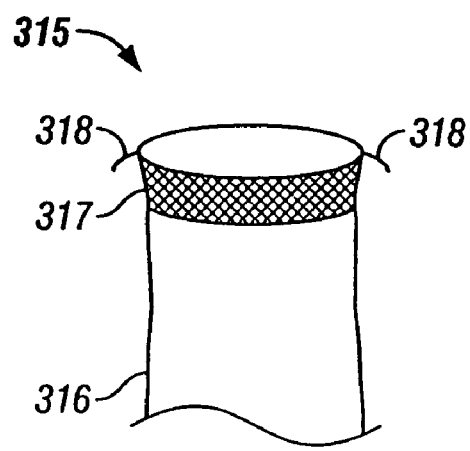

Another alternative variation to facilitate the anchoring of the bypass conduit may be seen in variation 315 in FIG. 15B. Conduit anchoring variation 315 may have a reinforced portion or section 317 located near or at the proximal end of conduit wall 316. This reinforced section 317 may comprise a radially expanding portion, much like a self-expanding stent made of a shape memory alloy such as nitinol; alternatively, section 317 may also comprise a prosthetic ring or gasket made of a polymeric material. Attachment points 318 may be optionally included to project from the proximal end of conduit wall 316 or from the reinforced section 317. These attachment points 318 may be configured to pierce into the tissue and aid in affixing the conduit 315 by helping to hold the conduit 315 securely in place along the tissue. The attachment points 318 may be positioned around the circumference of the conduit wall 316 or in any number of configurations as is known in the art. Although the figure shows attachments points 318 as hooks, any number of different configurations may be utilized, e.g., barbs, clamps, sutures, staples, stents, bands, adhesives, etc., may also be used.

Bypass Conduit Placement

Figure 16A:
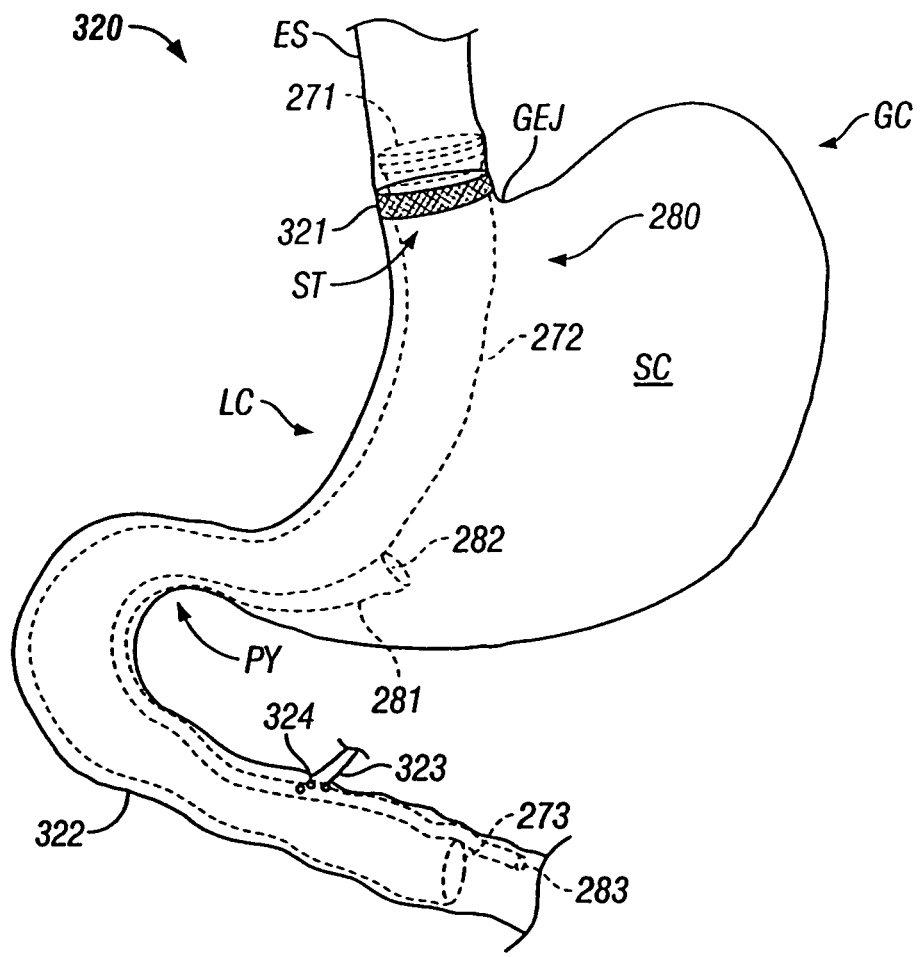
FIGS. 16A-16B depict a bypass conduit with a fluid bypass conduit deployed within a stoma created by a laparoscopic banding procedure.
Figure 16B:
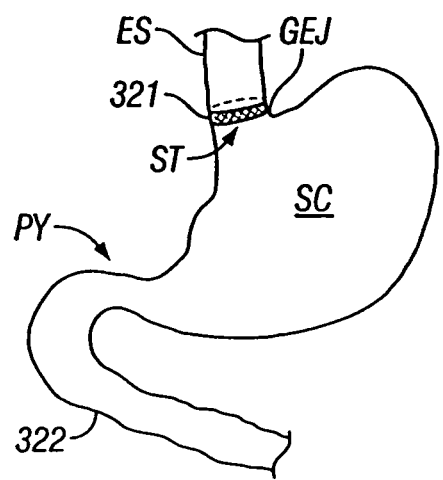

The bypass conduit may be positioned between the stomach cavity (SC) and the intestines in a variety of ways aside from that shown in FIG. 5E above. The bypass conduit assembly 280 may be used in conjunction with various gastric procedures. As seen in FIG. 16A, bypass conduit assembly 280 may be used with a stomach (SC) which has undergone a laparoscopic banding procedure. FIG. 16B shows a view of a lap band 321 which has been positioned around a portion of the stomach cavity (SC) below the esophagus (ES) prior to having a bypass conduit deployed. FIG. 16A shows a view of assembly 320 in which conduit assembly 280 has been positioned to extend from the stoma (ST) created by the banding, to a point past the pylorus (PY). As shown, the proximal end 271 of the conduit assembly 280 may be secured within the stoma created by the lap band 321 using any of the methods described above. The conduit wall 272 is appropriately sized such that it extends through the stomach cavity (SC) from, in this variation, the stoma (ST) into the intestines, e.g., the duodenum 322, although the distal end 273 may extend farther into the intestinal tract, e.g., to the jejunum. The distal end 273 of the conduit wall 272 may be left unanchored in the intestinal tract or it may be optionally anchored to the tissue. Anchoring of the distal end 273 may be achieved using any of the anchoring methods as described above for anchoring of the proximal end 271.

The fluid conduit 281 may be seen in this variation as being positioned along the conduit wall 272 and within the stomach cavity (SC) such that its proximal end 282 is placed within the stomach cavity (SC) at the stoma (ST) and its distal end 283 extends past the pylorus (PY) and partly into the duodenum. Although fluid conduit 281 may be sized to have a length that is shorter than the conduit wall 272, it may typically be sized to have a length which is longer than or coterminous with that of conduit wall 272, and further adapted to facilitate fluid communication between the stomach cavity (SC), or gastric remnant, and the intestines, or the duodenal ampulla 323 and the intestines. As positioned, fluid conduit 281 allows for the gastric fluids produced within the stomach cavity (SC) and the digestive fluids discharged through the duodenal ampulla (or duct) 323 to intermix and to be transported through the conduit 281 between the stomach cavity (SC) and the intestine distal of the duodenal ampulla 323. The fluid conduit 281 also allows for the fluids to intermix and for the fluids produced within the stomach cavity (SC) to drain without contacting any ingested foods transported through the bypass conduit 272. If the distal end 283 of the fluid conduit 281 extends past the duodenal ampulla 323, the region of the conduit 281 near or at the entrance to the duct 323 may define one or more fenestrations or openings 324 along its length. These fenestrations 324 may be positioned and sized appropriately such that they allow for the fluid communication between the duct 323 and the lumen of the fluid conduit 281.

Figure 17A:
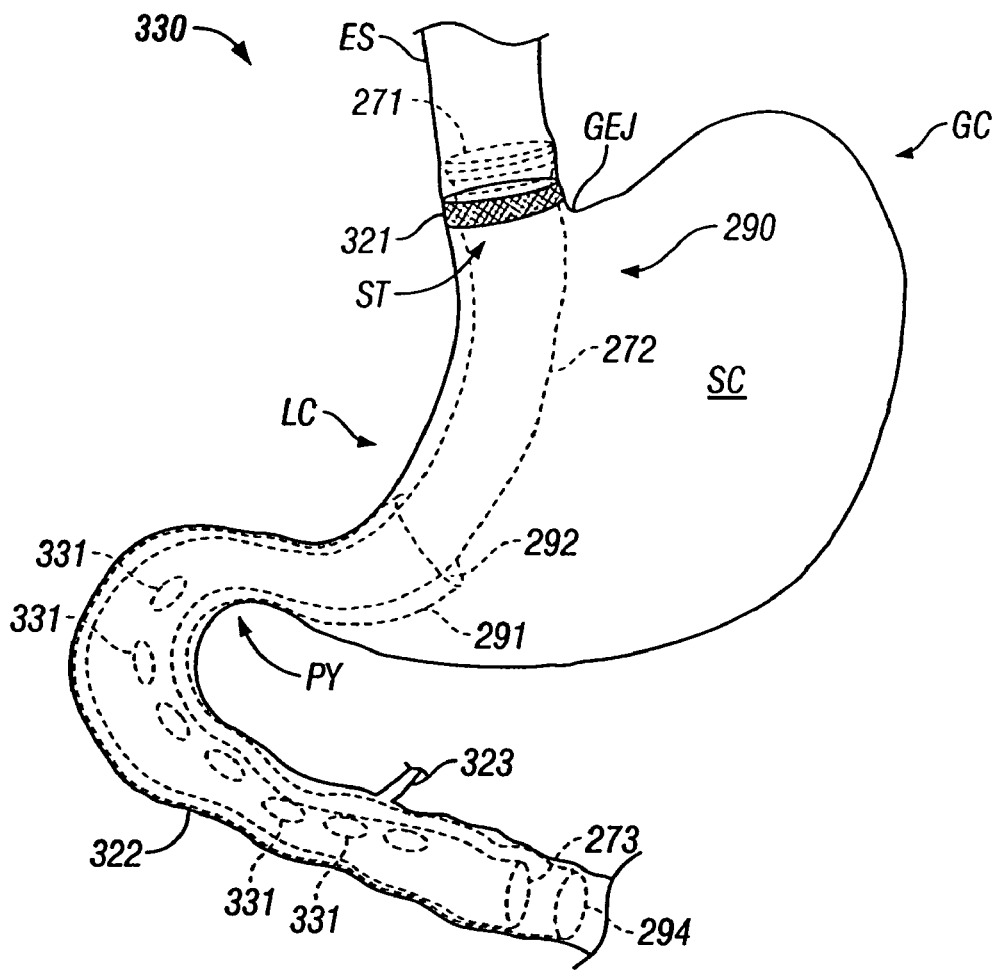
FIGS. 17A-17B depict a bypass conduit with a coaxial fluid bypass conduit deployed within a stoma created by a laparoscopic banding procedure.
Figure 17B:
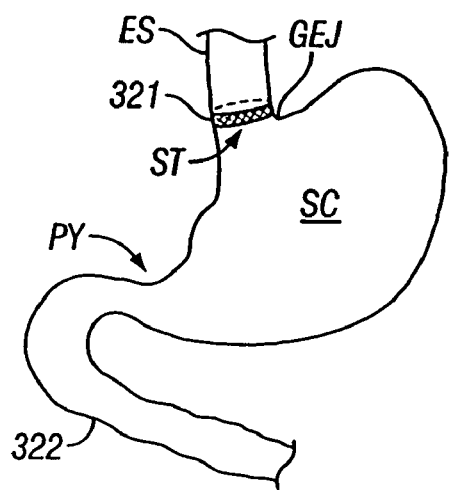

FIG. 17A shows another variation 330 utilizing the lap band 321 with the coaxial fluid bypass conduit 290. FIG. 17B shows a view of the stomach prior to having the conduit assembly 290 deployed. In this variation, fluid conduit 291 may be positioned such that its proximal end is within the stomach cavity (SC) and its distal end 294 is positioned within the duodenum 322 to the jejunum, either proximally of or at the duodenal ampulla 323. If the distal end 294 is positioned distally of the ampulla 323, one or more fenestrations 331 may be defined along the length of the fluid conduit 291 to facilitate the fluid exchange and to maintain the fluid communication, as described above, between the ampulla 323 and local intestine and the fluid conduit 291. The use of this coaxially adjacent conduit variation allows for the free rotation of the conduit wall 272 and/or fluid conduit 291 about its longitudinal axis within the stomach cavity (SC) without the problems of kinking or improper placement of the fluid conduit relative to the stomach cavity (SC). The proximal 271 and distal 273 ends of the conduit wall 272 may be anchored in much the same manner as described above.

Figure 18A:
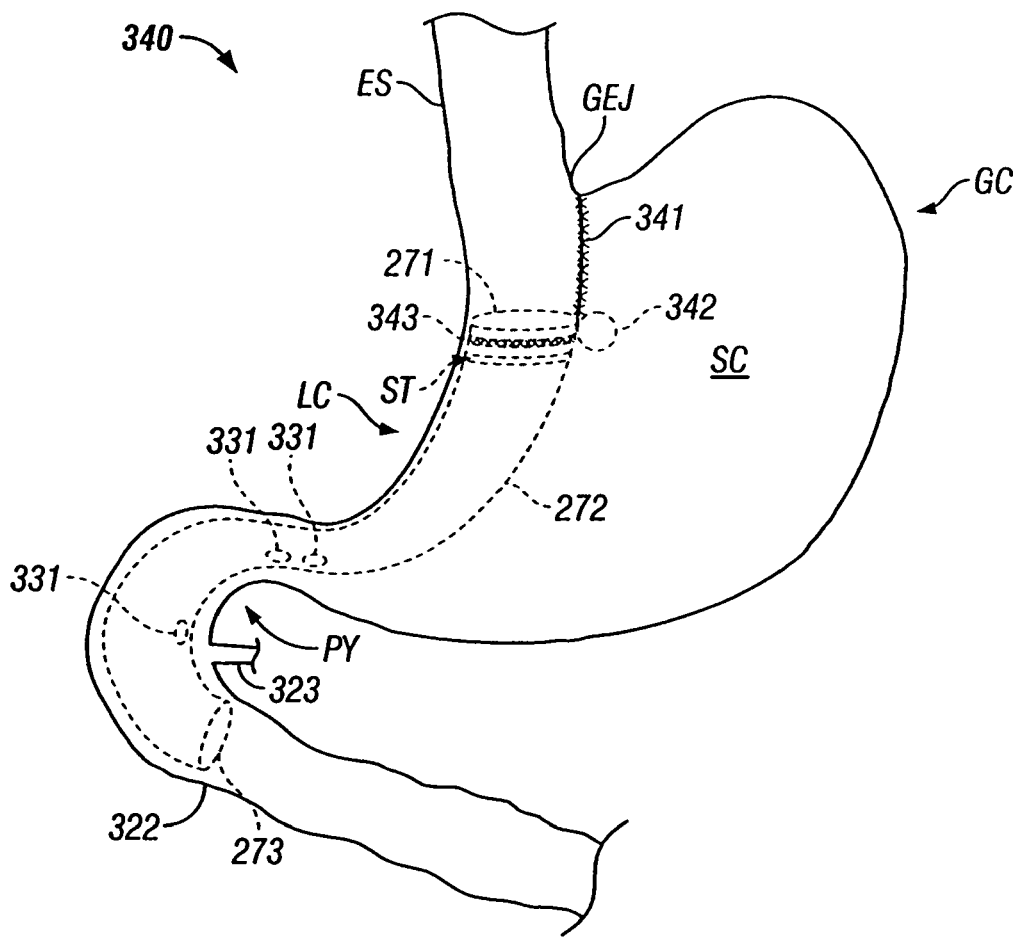
FIGS. 18A-18B depict a bypass conduit with spaced apart fenestrations deployed within a stoma created by a vertical banded gastroplasty procedure.
Figure 18B:
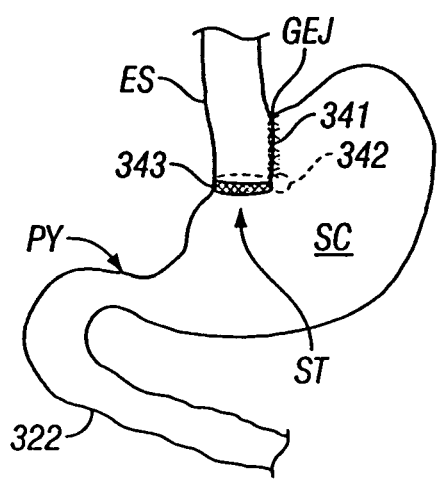

In the case of a stomach which has undergone a vertical banded gastroplasty (VBG) procedure, the conduit may also be utilized to facilitate patient treatment. FIG. 18B shows a view of the stomach which has had the VBG procedure prior to deployment of the bypass conduit. As shown, a vertical staple line 341 has been deployed along a portion of the stomach extending from the circular defect 342 defined within the stomach to the gastroesophageal junction (GEJ). A silastic band 343 has also been positioned to create a narrowing or stoma at the end of the staple line 341. As shown in the variation 340 of FIG. 18A, the bypass conduit 272 may be deployed such that its proximal end 271 is secured within the stoma (ST) created by placement of the silastic band 343 to bypass the stomach cavity (SC) and extend distally through the pylorus (PY), as described above. The conduit may thus extend from within the stomach cavity (SC) to within the intestinal tract. Moreover, one or more fenestrations 331 may be defined along certain portions of the length of the conduit wall 272 positioned at active secretory zones (such as within the stomach cavity (SC) and/or the duodenal ampulla) to allow fluid exchange through the walls of the bypass conduit 272 at the point of those anatomic structures. By spacing fenestrations 331, and limiting them to communication with only specified active zones, a single conduit construction can function both as a sufficient barrier between ingested food and the intestine (malabsorption), and a selected flowpath for digestive fluids.

Figure 19A:
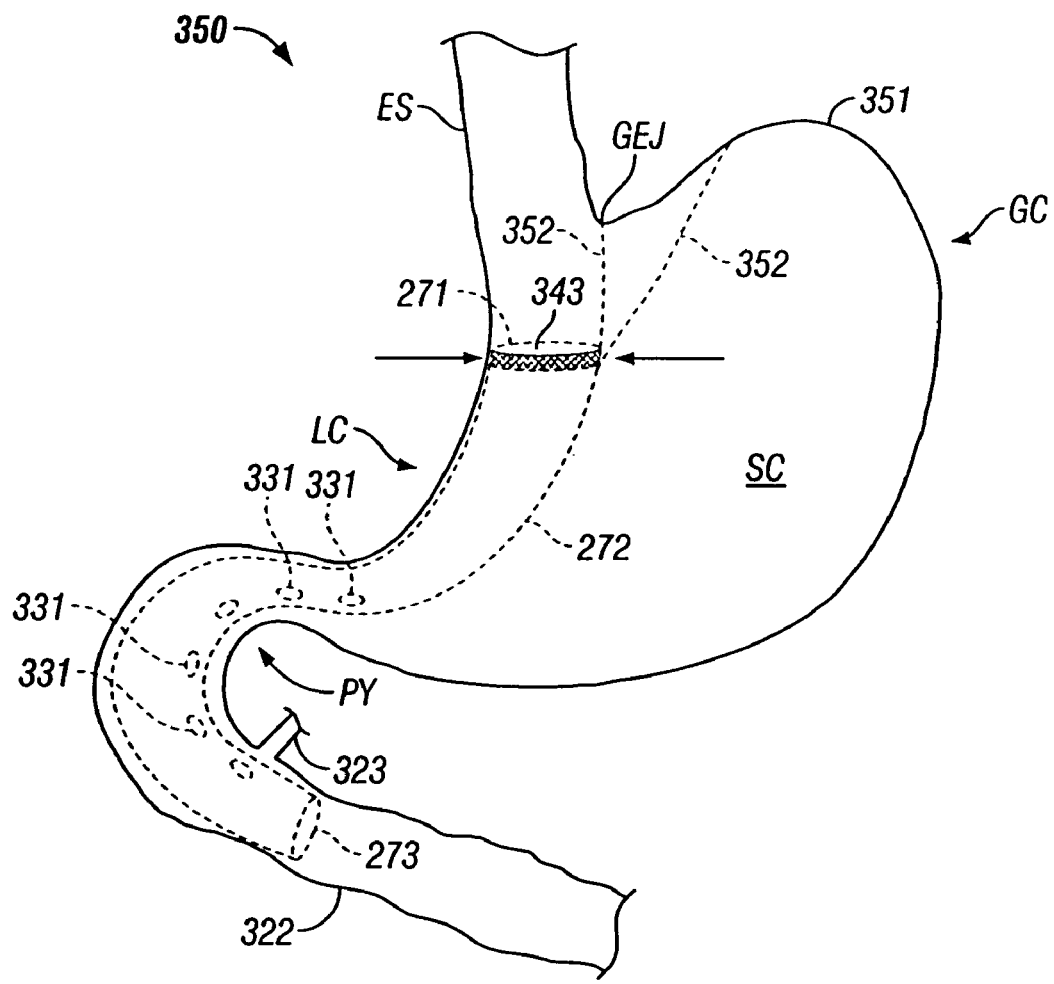
FIGS. 19A-19B depict a bypass conduit having valved fenestrations deployed within a stoma created by laparoscopic banding to constrict the stomach cavity and create a stoma.
Figure 19B:
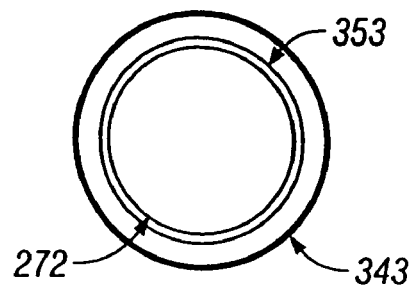
Figure 19C:
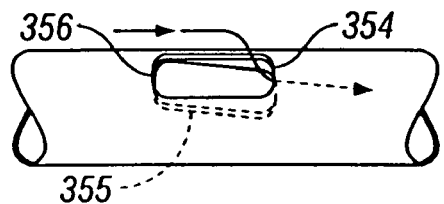
FIGS. 19C-19F depict variations on maintaining fluid communication through or along the bypass conduit.
Figure 19D:
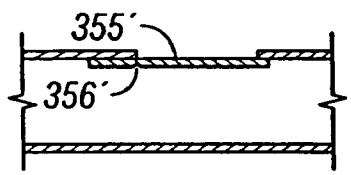
Figure 19E:
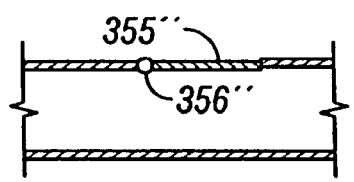
Figure 19F:
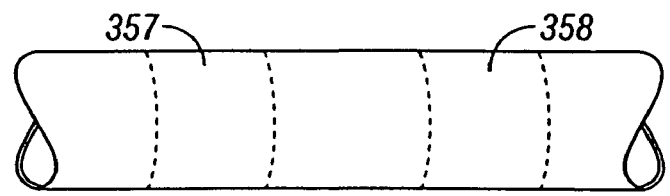

FIG. 19A shows another variation 350 in which a bypass conduit may be used with a stomach which has undergone laparoscopic banding to constrict the stomach cavity (SC) and create a stoma. The lap band 343 may be used to constrict the stomach such that the original stomach, as indicated by the outline 351, is constricted by the band 343 to create a constricted stomach, as indicated by the constricted outline 352. The bypass conduit proximal end 271 may then be secured within the stoma created by the lap band 343, as described above. Furthermore, fenestrations 331, which may be valved, may be placed along the length of the bypass conduit 272 to allow a single conduit to perform the dual functions of malabsorption and the maintenance of digestive fluid flow. Such fenestrations may include one-way valves that open to receive fluids from outside the bypass conduit. The valves may be configured to selectively open at regions along the conduit length where the pressure from such flow overcomes the force which maintains the valve closed; adequate pressure from the flow may be generated by the fluids such as within the gastric remnant or at the inflow of the ducts (duodenal ampulla). Such a design would not require specific alignment at flow inlets. FIG. 19C depicts one variation of a one-way valve 354 having a door or flap 355 hinged or partially secured at 356 to the inside of bypass conduit wall 272. Flap 355 may be biased to urge the valve shut in the absence of the fluid flow. FIGS. 19D and 19E are illustrative examples which show variations on the flap 355. FIG. 19D shows a flap 355' which may be attached to the conduit wall and hinged via notched section 356' about which flap 355' may rotate. FIG. 19E shows another example in which flap 355" may be attached about a biased hinge 356". In either case, these examples are merely intended to be illustrative and other methods of flap actuation are intended to be included herein. In addition, such selective communication between bypass conduit 272 and related organs or intestine can be established by varying the porosity or permeability of certain segments 357, 358 along the length of bypass conduit wall 272, as shown in FIG. 19F. FIG. 19B shows a cross-sectional view of the bypass conduit wall 272 secured to the stomach wall 353 by the lap band 343.

Figure 20A:
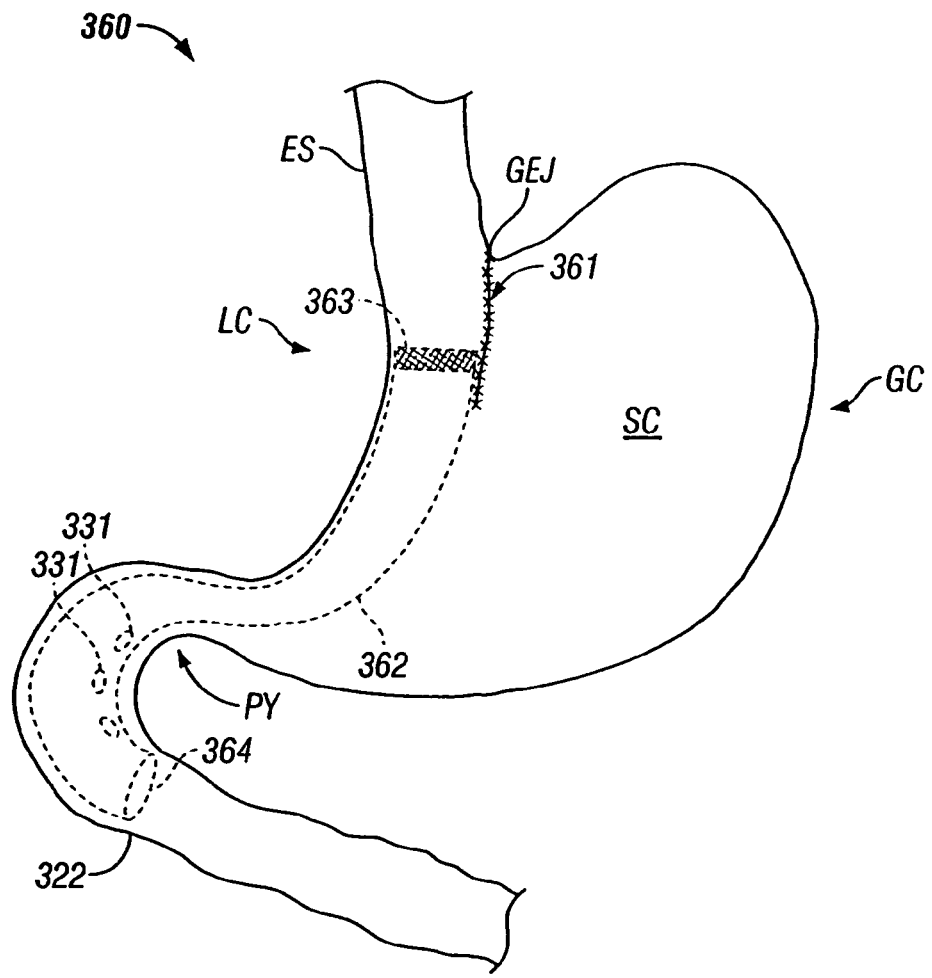
FIGS. 20A-20B depict a bypass conduit deployed within a stomach which has an intragastric staple line.
Figure 20B:
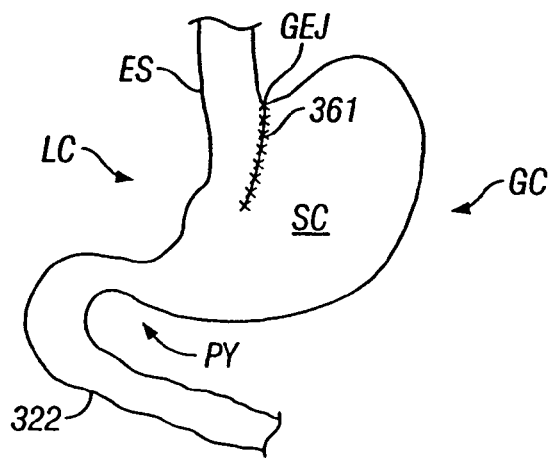

Another variation on conduit placement may be seen in conjunction with an intragastric stapling procedure in the variation 360 in FIG. 20A. FIG. 20B shows a view of the stomach in which an intragastric stapling procedure has been performed to create an intragastric staple line 361. To affix a bypass conduit 362 near or at the end of the staple line 361, conduit 362 may utilize an anchor region 363, or stoma, which may use any of the various anchoring methods described above. For instance, any number of fasteners, e.g., hooks, barbs, clamps, sutures, staples, stents, bands, adhesives, etc., may be used although FIG. 20A shows an anchor configured as a stent. The anchor region 363 may be placed anywhere along the staple line 361 so long as the anchor region 363 may be securely affixed between the staple line 361 and the stomach tissue. The distal end 364 of the conduit 362 may remain unanchored or it may be optionally anchored to the tissue within the duodenum 322, as described above.

Figure 21A:
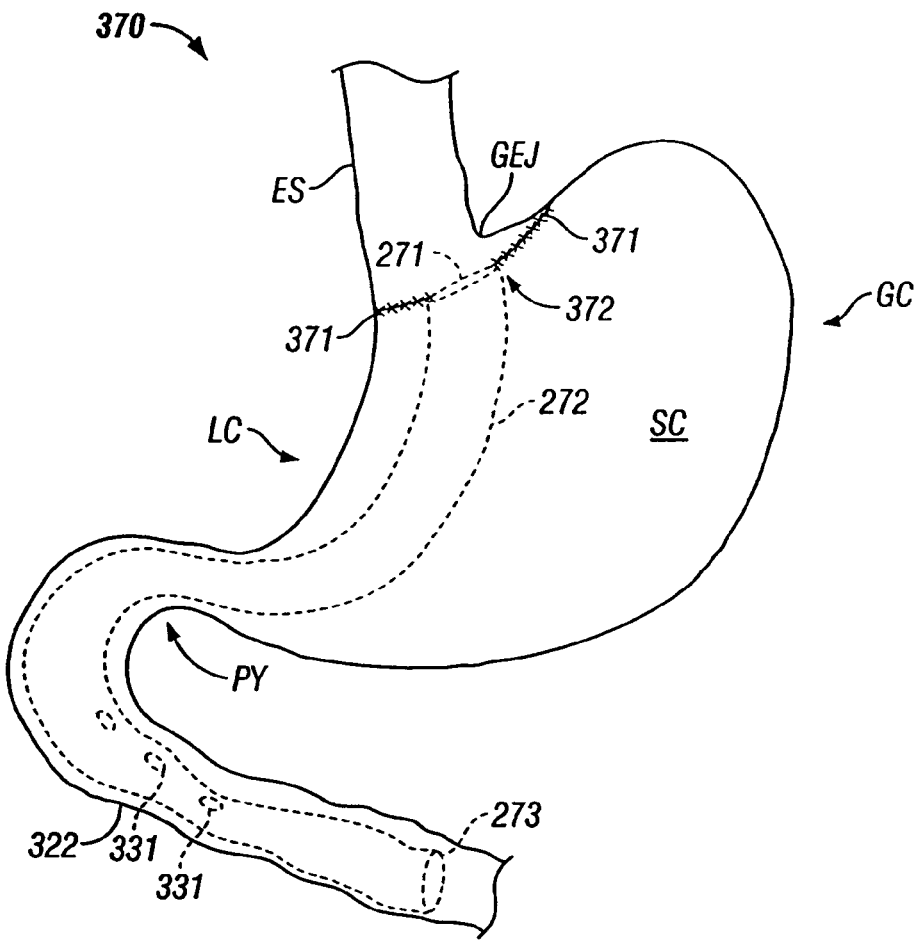
FIGS. 21A-21B depict a bypass conduit deployed within a stoma created by a horizontal gastroplasty procedure.
Figure 21B:
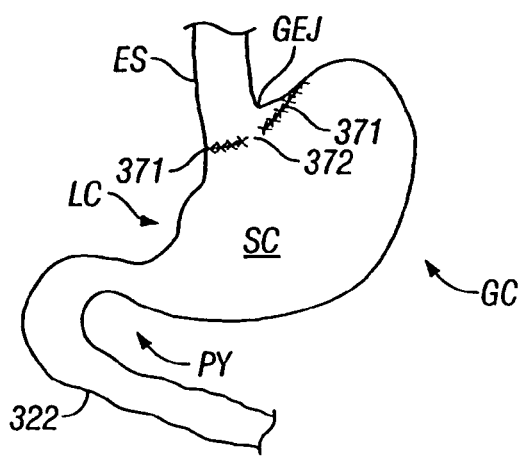

Yet another variation on conduit placement may be seen in the variation 370 in FIG. 21A. FIG. 21B shows a view of the stomach that has undergone a horizontal gastroplasty procedure in which a horizontal staple line 371 is created extending from the lesser curvature (LC) to the greater curvature (GC) of the stomach. A portion of the stomach may be left unstapled to create a stoma 372 between the esophagus and the remainder of the stomach cavity (SC). The proximal end 271 of the bypass conduit 272 may be secured within this stoma 372 using any of the attachment methods as described above.

Figure 22A:
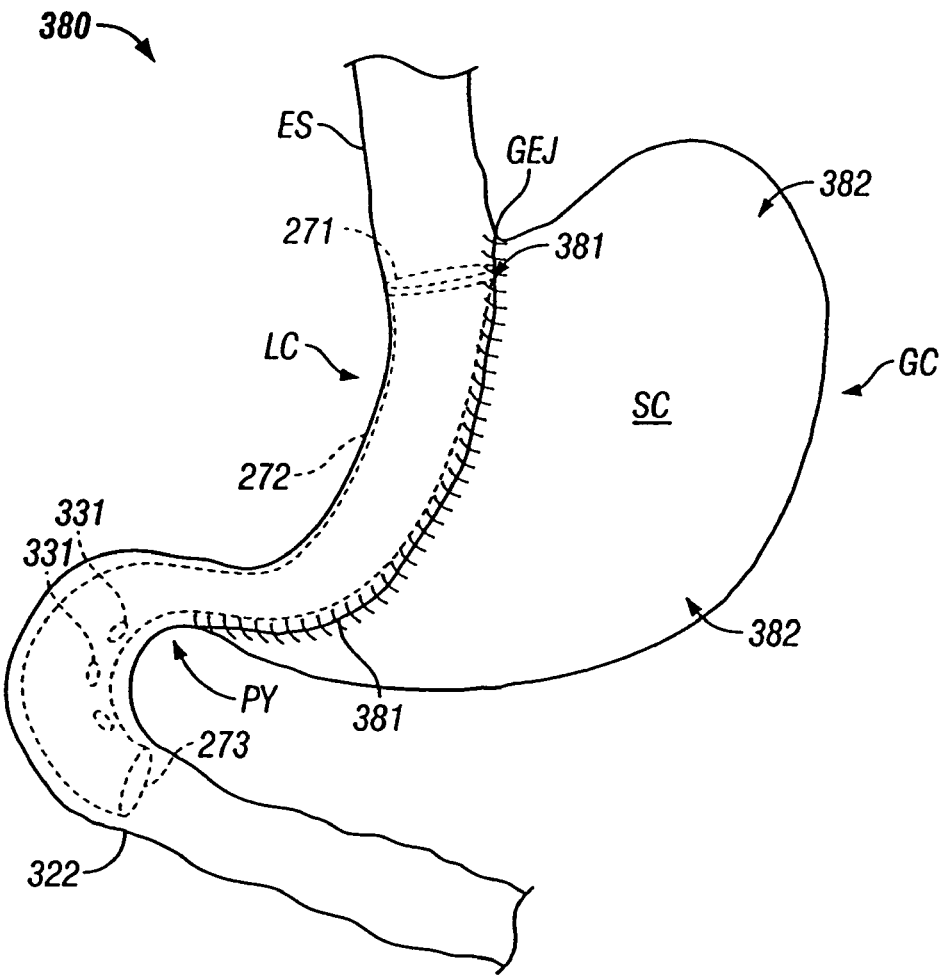
FIGS. 22A-22B depict a bypass conduit deployed within a stoma created by a biliopancreatic diversion procedure.
Figure 22B:
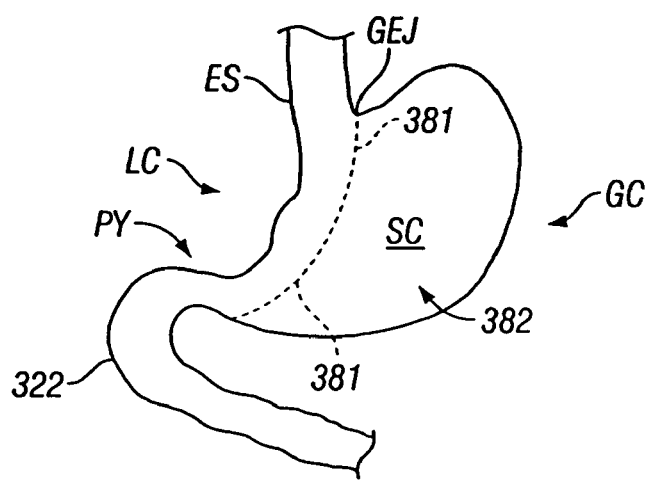

Another variation may be seen in variation 380 in FIG. 22A. In this variation, the stomach has undergone a biliopancreatic diversion (BPD) procedure where a small portion of the stomach is partitioned off and the remaining portion of the stomach may be left or removed. A BPD procedure is similar to a Jejuno-Ileal Bypass (JIB) procedure in which a large portion, i.e., about two-thirds, of the stomach is partitioned off and/or removed. FIG. 22B shows a view of a stomach which has been partitioned along a staple line 381, which may roughly parallel the lesser curvature (LC) of the stomach extending from the gastroesophageal junction (GEJ) to near the pylorus (PY). The partitioned-off portion 382 may optionally be removed leaving the portion of the stomach extending from the esophagus (ES) directly to the pylorus (PY). Within the remaining portion of stomach, the bypass conduit 272 may be positioned such that its proximal end 271 is secured near or at the gastroesophageal junction (GEJ), using any of the methods described above, and the distal end 273 may be routed distal of the stomach into the intestinal tract where it may be unanchored or secured to the tissue.

Yet another variation on conduit placement may include the use of conventional devices such as those described in U.S. Pat. No. 4,458,681 (Hopkins) and in U.S. Pat. No. 4,558,699 (Bashour), which are both incorporated herein by reference in their entirety. Both patents describe variations on clamps which may be placed across a stomach (externally) to create a stoma therewithin for the passage of food through the stomach. The clamps may be placed over the stomach, e.g., through conventional laparoscopic procedures, and a bypass conduit may be placed endoscopically within the stomach such that the proximal end of the conduit is supported by the clamp within the created stoma using any of the methods described above.

The steps of performing the method of organ division or reduction (transoral stomach reduction) are used to illustrate in detail the method and devices of the present invention, however the present invention is not limited thereby. Use of these steps and the tools deployed therein may be varied to achieve a similar result in other hollow body organs and it is anticipated that such techniques can be employed to divide or restrict other hollow body organs such as organs of the gastrointestinal tract such as bowel, stomach or intestine, or in procedures in the bladder (treatment for incontinence by reinforcing the bladder sphincter) or uterus, etc. In addition, as previously mentioned, other procedures such as the treatment of GERD may also benefit from the methods and devices disclosed herein. While certain embodiments have been illustrated and described in detail, those having ordinary skill in the art will appreciate that various alternatives, modifications, and equivalents may be used and that the invention is not intended to be limited to the specifics of these variations.

We claim:

1. A system for bypassing a hollow body organ, comprising:
   a tissue approximation and fixation apparatus having an elongate outer tubular member defining at least a first lumen therethrough, the elongate outer tubular member having a plurality of rings, the rings having one or more pivots for facilitating relative motion therebetween, and an elongate inner tubular member defining at least a second lumen therethrough and slidingly disposed throughout the first lumen such that a distal portion of the inner tubular member extends partially beyond a distal end of the outer tubular member, and the tissue approximation and fixation apparatus having a fastening device attached to the distal end of the inner tubular member, wherein the fastening device defines a circumferential receiving surface about the inner tubular member, and wherein the fastening device further defines at least one port in fluid communication with the second lumen of the inner tubular member, wherein an enclosable channel is defined about the distal portion of the inner tubular member when the receiving surface of the fastening device is positioned adjacently to the distal end of the outer tubular member;
   a bypass conduit having a tubular member with a proximal end and a distal end which defines a main lumen therethrough, wherein the main lumen maintains communication from proximal to distal of the hollow body organ, and wherein at least a portion of an outer surface of the tubular member is adapted to maintain fluid communication therealong;
   wherein the tissue approximation and fixation device forms a narrowed region within the hollow body organ and the bypass conduit is affixed to the narrowed region of the hollow body organ.

2. The system of claim 1, wherein the outer surface of the tubular member of the bypass conduit defines at least one channel along at least the portion of the outer surface.

3. The system of claim 2, wherein the at least one channel of the bypass conduit maintains fluid communication between the hollow body organ and a region distal of the hollow body organ through the at least one channel of the bypass conduit.

4. The system of claim 2, wherein the tubular member of the bypass conduit further defines a plurality of additional channels along the outer surface of the tubular member of the bypass conduit.

5. The system of claim 2, wherein the at least one channel of the bypass conduit extends between the hollow body organ and a region distal of the hollow body organ.

6. The system of claim 2, wherein the at least one channel of the bypass conduit extends between a first region distal of the hollow body organ and a second region distal of the first region.

7. The system of claim 2, wherein the at least one channel of the bypass conduit extends along a length of the tubular member of the bypass conduit.

8. The system of claim 2, wherein the at least one channel of the bypass conduit is defined longitudinally along the outer surface of the tubular member of the bypass conduit.

9. The system of claim 1, further comprising one or more cables coupled to the elongate outer tubular member and configured to control locations of the plurality of rings.

10. The system of claim 1, wherein the receiving surface of the fastening device is formed at an angle relative to a longitudinal axis of the elongate outer tubular member and the distal end of the outer tubular member is formed at a complimentary angle to the angle of the receiving surface of the fastening device.

11. The system of claim 1, wherein one or more of: the fastening device, a distal portion of the elongate inner tubular member, and a distal portion of the elongate outer tubular member further comprises a plurality of ports formed thereon.

* * * * *